US012006328B2

(12) United States Patent
Traynelis et al.

(10) Patent No.: US 12,006,328 B2
(45) Date of Patent: Jun. 11, 2024

(54) THIENO[2,3-D]PYRIMIDIN-4-ONE DERIVATIVES AS NMDAR MODULATORS AND USES RELATED THERETO

(71) Applicant: Emory University, Atlanta, GA (US)

(72) Inventors: Stephen F. Traynelis, Decatur, GA (US); Lanny S. Liebeskind, Atlanta, GA (US); Dennis C. Liotta, Atlanta, GA (US); Ethel C. Garnier-Amblard, Tucker, GA (US); PavanKumar Reddy Gangireddy, Atlanta, GA (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 15/528,087

(22) PCT Filed: Nov. 18, 2015

(86) PCT No.: PCT/US2015/061418
§ 371 (c)(1),
(2) Date: May 18, 2017

(87) PCT Pub. No.: WO2016/081649
PCT Pub. Date: May 26, 2016

(65) Prior Publication Data
US 2017/0313719 A1 Nov. 2, 2017

Related U.S. Application Data

(60) Provisional application No. 62/081,050, filed on Nov. 18, 2014.

(51) Int. Cl.
*C07D 495/04* (2006.01)
*A61P 25/16* (2006.01)
*A61P 25/18* (2006.01)
*A61P 25/22* (2006.01)
*A61P 25/28* (2006.01)

(52) U.S. Cl.
CPC ............ *C07D 495/04* (2013.01); *A61P 25/16* (2018.01); *A61P 25/18* (2018.01); *A61P 25/22* (2018.01); *A61P 25/28* (2018.01)

(58) Field of Classification Search
CPC .................................................. A61K 31/519
See application file for complete search history.

(56) References Cited

U.S. PATENT DOCUMENTS

| 10,500,205 | B2 | 12/2019 | Anderson | |
|---|---|---|---|---|
| 2007/0208040 | A1 | 9/2007 | Elzein | |
| 2008/0280900 | A1 | 11/2008 | Pajouhesh | |
| 2009/0111835 | A1 | 4/2009 | Nakazato | |
| 2009/0131455 | A1 | 5/2009 | Gallagher | |
| 2009/0163545 | A1* | 6/2009 | Goldfarb | A61K 31/13 |
| | | | | 514/688 |

FOREIGN PATENT DOCUMENTS

| EP | 640606 | * | 3/1995 | |
|---|---|---|---|---|
| JP | 56008389 | * | 1/1981 | |
| WO | WO-2013188848 A2 | * | 12/2013 | ......... A61K 31/4184 |

OTHER PUBLICATIONS

Stella (J. Pharmaceutical Sciences, 2010, 99(12), pp. 4755-4765).*
STN printout (FCH Group, Registry #1288144-55-7, May 1, 2011, downloaded Sep. 23, 2017).*
Hosni et al. (J. Chem. Research, 1999, vol. 11, pp. 646-647).*
Bode et al. (J. Ethnopharmcol., 1996, vol. 50, pp. 103-113).*
Kotei et al. (Ukrainica Biororganic Acta, 2008, vol. 6(2), pp. 3-9).*
STNext answer 87 of 98, Registry No. 691386-78-4, Jun. 10, 2004, downloaded Jul. 11, 2020, pp. 1-2.*
STNext answer 6 of 10, Registry No. 877449-93-9, Mar. 21, 2006, downloaded Jul. 11, 2020, p. 1.*
STNext answer 88 of 98, Registry No. 691386-61-5, Jun. 10, 2004, downloaded Jul. 11, 2020, p. 1.*
STNext answer 44 of 58, Registry No. 1287608-73-4, Apr. 29, 2011, p. 1.*
STNext answer 1066 of 1097, Registry No. 804514-62-3, Dec. 12, 2004, p. 1.*
STNext answer 597 of 735, Registry No. 920920-69-0, Feb. 14, 2007, p. 1.*
STNext answer 494 of 620, Registry No. 930539-89-2, Apr. 17, 2007, p. 1.*
STNext answer 1090 of 1097, Registry No. 457918-44-4, Oct. 2, 2002, p. 1.*
STNext answer 42 of 53, Registry No. 691386-61-5, Jun. 10, 2004, p. 1.*
PubChem database (PubChem CID 1192581, <https://pubchem.ncbi.nlm.nih.gov/compound/1192581#section=BioAssay-Results&fullscreen=true> downloaded Apr. 13, 2022, pp. 1-2).*
Di Fruscia et al., The Discovery of a Highly Selective 5,6,7,8-Tetrahydrobenzo[4,5]thieno[2,3-d]pyrimidin-4(3H)-one SIRT2 Inhibitor that is Neuroprotective in an in vitro Parkinson's Disease Model, ChemMedChem, 2015, 10(1), 69-82.
Golub et al., Synthesis and biological evaluation of substituted (thieno[2,3-d]pyrimidine-4-ylthio)carboxylic acids as Inhibitors of human protein kinase CK2, Eur J Med Chem, 2011, 46 870-876.
Rashad et al., Synthesis and screening of some novel fused thiophene and thienopyrimidine derivatives for anti-avian Influenza virus (H5N1) activity, Eur J Med Chem, 2010, 45, 5252-5257.
Wang et al., A novel NMDA receptor positive allosteric modulator that acts via the transmembrane domain, Neuropharmacology, 2017, 121, 204-218.
AKos Consulting & Solutions, Vendor Reference ID: AKOS016522720, 2014.
ChemBridge, Vendor Reference ID: 7788789, 2005.
ChemBridge, Vendor Reference ID: 7981948, 2005.
ChemBridge, Vendor Reference ID: 7643946, 2005.

(Continued)

*Primary Examiner* — Susanna Moore
(74) *Attorney, Agent, or Firm* — Emory Patent Group

(57) ABSTRACT

The disclosure relates thieno[2,3-d]pyrimidin-4-one derivatives as modulators of NMDA receptors and uses related thereto. In certain embodiments, the disclosure relates to pharmaceutical compositions comprising compounds disclosed herein or pharmaceutically acceptable salts or prodrugs thereof. In certain embodiments, the compositions disclosed herein are used for managing conditions related to cognition, typically prevention or treatment of neurological conditions related to the NMDA receptor.

26 Claims, 1 Drawing Sheet

(56) References Cited

OTHER PUBLICATIONS

Discoverygate, Deposit ID 43027833, 2010.
MolPort, Vendor Reference ID: MolPort-004-457-609, 2010.
MolPort, Vendor Reference ID: MolPort-004-195-871, 2010.
MolPort, Vendor Reference ID: MolPort-004-122-392, 2010.
MolPort, Vendor Reference ID: MolPort-004-060-846, 2010.
MolPort, Vendor Reference ID: MolPort-004-067-297, 2010.
MolPort, Vendor Reference ID: MolPort-000-671-865, 2010.
MolPort, Vendor Reference ID: MolPort-000-670-035, 2010.
MolPort, Vendor Reference ID: MolPort-000-671-531, 2010.
PubChem, PubChem CID: 2532899, 2005.
PubChem, PubChem CID: 2532904, 2005.
PubChem, PubChem CID: 1669137, 2005.
PubChem, PubChem CID: 1671380, 2005.
PubChem, PubChem CID: 23410493, 2007.
PubChem, PubChem CID: 40942517, 2009.
PubChem, PubChem CID: 40942518, 2009.
PubChem, PubChem CID: 27353527, 2009.
Zinc, Vendor Reference ID: ZINC22357299, 2009.
Zinc, Vendor Reference ID: ZINC22357301, 2009.
Zinc, Vendor Reference ID: ZINC13164338, 2009.
Zinc, Vendor Reference ID: ZINC13164337, 2009.
Zinc, Vendor Reference ID: ZINC13014066, 2009.
Zinc, Vendor Reference ID: ZINC13014063, 2009.
PubChem CID 1192581, SiD 14746351, BioAssay Results p. 5 of 783, available at https://pubchem.ncbi.nlm.nih.gov/compound/1192581 #section=BioAssay-Results&fullscreen=true, downloaded Sep. 23, 2022.

* cited by examiner

| Compound Structure | Identifier | Subunit | EC50 (µM) | Maximum Potentiation (% of Control) |
|---|---|---|---|---|
| 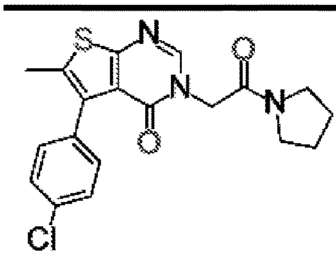 | 1622 | 2A | -- | -- |
| | | 2B | 10.8 ± 1.3 | 223 ± 7% |
| 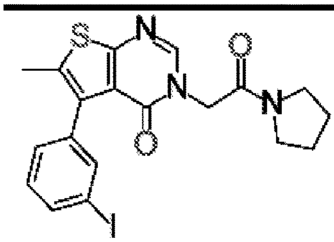 | 1622-35 | 2A | -- | -- |
| | | 2B | 4.4 ± 0.9 | 292 ± 13% |

THIENO[2,3-D]PYRIMIDIN-4-ONE DERIVATIVES AS NMDAR MODULATORS AND USES RELATED THERETO

CROSS-REFERENCE TO RELATED APPLICATIONS

This Application is the National Stage of International Application Number PCT/US2015/061418 filed Nov. 18, 2015, which claims priority to U.S. Provisional Application No. 62/081,050 filed Nov. 18, 2014. The entirety of each of these applications is hereby incorporated by reference for all purposes.

STATEMENT REGARDING FEDERALLY FUNDED RESEARCH

This invention was made with government support under R21MH094525 and R01NS065371 awarded by NIMH and NINDS respectively. The government has certain rights in the invention.

BACKGROUND

N-Methyl-D-Aspartate Receptors (NMDARs) typically contain a GluN1 subunit in addition to GluN2A-GluN2D subunits. Stimulation of one or more of the subunits are thought to be beneficial for the treatment of cognitive dysfunctions as well as other conditions dependent on synaptic plasticity such as motor retraining and rehabilitation after ischemic insult, traumatic brain injury, and conditions that involve impairment of movement, speech, vision, or other functions controlled by the brain. See Traynelis et al., Glutamate receptor ion channels: structure, regulation, and function. Pharmacol Rev, 2010, 62:405-496. See also Hardingham & Bading, Synaptic versus extrasynaptic NMDA receptor signaling: implications for neurodegenerative disorders, Nat Rev, Neurosci, 2010, 11:682-696; Tang et al., Genetic enhancement of learning and memory in mice, Nature, 401, 63-69 (1999); and Brigman et al., Loss of GluN2B-containing NMDA receptors in CA1 hippocampus and cortex impairs long-term depression, reduces dendritic spine density, and disrupts learning. J Neurosci, 2010, 30, 4590-4600.

Rashad et al. report synthesis and screening of fused thiophene and thienopyrimidine derivatives for anti-avian influenza virus (H5N1) activity. Eur J Med Chem, 2010, 45(11):5251-7. Golub et al. report substituted (thieno[2,3-d]pyrimidin-4-ylthio)carboxylic acids as inhibitors of human protein kinase CK2. Eur J Med Chem, 2011, 46:870e876. DiFruscia et al. report a 5,6,7,8-tetrahydrobenzo[4,5]thieno[2,3-d]pyrimidin-4(3H)-one SIRT2 inhibitor that is neuroprotective in an in vitro Parkinson's disease model, ChemMed Chem, 2015, 10(1):69-82. See also US 20080280900, CAS Registry Numbers 685844-76-2 and 791082-46-7.

References cited herein are not an admission of prior art.

SUMMARY

The disclosure relates to thieno[2,3-d]pyrimidin-4-one derivatives as modulators of NMDA receptors and uses related thereto. The disclosure relates to pharmaceutical compositions comprising compounds disclosed herein, derivatives, prodrugs, esters, or salts thereof. For example, the disclosure relates to compounds comprising Formula I,

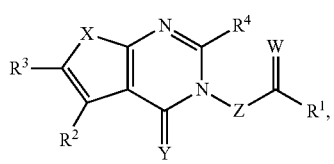

Formula I derivatives, prodrugs, esters, or salts thereof wherein, wherein the substituents are described herein.

The disclosure further relates to pharmaceutical compositions comprising a compound as reported herein and a pharmaceutically acceptable excipient. In certain embodiments, the pharmaceutical composition is in the form of a tablet, capsule, pill, gel, solid formulation comprising a saccharide, polysaccharide, or fatty acid, a pH buffered solution, or a solution containing an alcohol or oil.

Also, the disclosure relates to methods of treating or preventing a neurological disease, condition, or disorder comprising administering an effective amount of a compound disclosed herein to a subject in need thereof. For example, the condition is depression, anxiety, schizophrenia, or bipolar disorder.

Optionally, the condition is a central nervous system (CNS) disorder such as those selected from Alzheimer's disease, Huntington's disease, and Amyotrophic Lateral Sclerosis (ALS). The disclosure further relates to methods of improving learning or memory comprising administering an effective amount of a compound disclosed herein to a subject in need thereof.

The disclosure relates to methods of improving recovery and retraining after a CNS injury comprising administering an effective amount of a compound disclosed herein to a subject in need thereof. By way of example, the CNS injury is traumatic brain injury, stroke, hypoxia, cognitive deficits following coronary artery bypass grafting, or spinal cord injury.

The disclosure provides methods of preparing compounds disclosed herein comprising mixing the starting materials with reagents disclosed herein under conditions such that the products are formed.

DETAILED DESCRIPTION

Figure 1A:
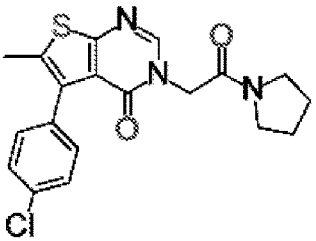
FIG. 1A shows activity data for compounds 1622 and 1622-35.
Figure 1A:
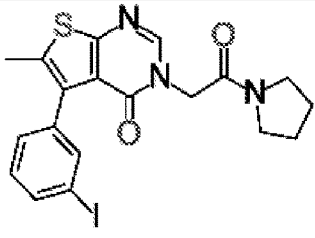

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. In this specification and in the claims that follow, reference will be made to a number of terms that shall be defined to have the following meanings unless a contrary intention is apparent.

Prior to describing the various embodiments, the following definitions are provided and should be used unless otherwise indicated.

To the extent that structures provided herein are compounds with tautomers by hydrogen migration, a skilled artisan would understand the formula to cover all tautomeric forms.

As used herein, "alkyl" means a noncyclic straight chain or branched, unsaturated or saturated hydrocarbon such as those containing from 1 to 10 carbon atoms, typically 1 to 4 otherwise designated $C_{1-4}$alkyl. Representative saturated straight chain alkyls include methyl, ethyl, n-propyl, n-butyl, n-pentyl, n-hexyl, n-septyl, n-octyl, n-nonyl, and the like; while saturated branched alkyls include isopropyl, sec-butyl, isobutyl, tert-butyl, isopentyl, and the like. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

Non-aromatic mono or polycyclic alkyls are referred to herein as "carbocycles" or "carbocyclyl" groups. Representative saturated carbocycles include cyclopropyl, cyclobutyl, cyclopentyl, cyclohexyl, and the like; while unsaturated carbocycles include cyclopentenyl and cyclohexenyl, and the like.

"Heterocarbocycles" or heterocarbocyclyl" groups are carbocycles which contain from 1 to 4 heteroatoms independently selected from nitrogen, oxygen and sulfur which may be saturated or unsaturated (but not aromatic), monocyclic or polycyclic, and wherein the nitrogen and sulfur heteroatoms may be optionally oxidized, and the nitrogen heteroatom may be optionally quaternized. Heterocarbocycles include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydropyrimidinyl, tetrahydrothiophenyl, tetrahydrothiopyranyl, tetrahydropyrimidinyl, tetrahydrothiophenyl, tetrahydrothiopyranyl, and the like.

The term "aryl" refers to aromatic homocyclic (i.e., hydrocarbon) mono-, bi- or tricyclic ring-containing groups preferably having 6 to 12 members such as phenyl, naphthyl and biphenyl. Phenyl is a preferred aryl group. The term "substituted aryl" refers to aryl groups substituted with one or more groups, preferably selected from alkyl, substituted alkyl, alkenyl (optionally substituted), aryl (optionally substituted), heterocyclo (optionally substituted), halo, hydroxy, alkoxy (optionally substituted), aryloxy (optionally substituted), alkanoyl (optionally substituted), aroyl, (optionally substituted), alkylester (optionally substituted), arylester (optionally substituted), cyano, nitro, amino, substituted amino, amido, lactam, urea, urethane, sulfonyl, and, the like, where optionally one or more pair of substituents together with the atoms to which they are bonded form a 3 to 7 member ring.

As used herein, "heteroaryl" or "heteroaromatic" refers an aromatic heterocarbocycle having 1 to 4 heteroatoms selected from nitrogen, oxygen and sulfur, and containing at least 1 carbon atom, including both mono- and polycyclic ring systems. Polycyclic ring systems may, but are not required to, contain one or more non-aromatic rings, as long as one of the rings is aromatic. Representative heteroaryls are furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl. It is contemplated that the use of the term "heteroaryl" includes N-alkylated derivatives such as a 1-methylimidazol-5-yl substituent.

As used herein, "heterocycle" or "heterocyclyl" refers to mono- and polycyclic ring systems having 1 to 4 heteroatoms selected from nitrogen, oxygen and sulfur, and containing at least 1 carbon atom. The mono- and polycyclic ring systems may be aromatic, non-aromatic or mixtures of aromatic and non-aromatic rings. Heterocycle includes heterocarbocycles, heteroaryls, and the like.

"Alkylthio" refers to an alkyl group as defined herein attached through a sulfur bridge. An example of an alkylthio is methylthio, (i.e., —S—$CH_3$).

"Alkoxy" refers to an alkyl group as defined herein attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, i-propoxy, n-butoxy, s-butoxy, t-butoxy.

"Alkylamino" refers an alkyl group as defined herein attached through an amino bridge. An example of an alkylamino is methylamino, (i.e., —NH—$CH_3$).

"Aminoalkyl" refers to an amino group attached through an alkyl bridge as defined herein (i.e., $NH_2$-alkyl-).

"Alkanoyl" refers to an alkyl as defined herein attached through a carbonyl bridge (i.e., —(C═O)alkyl).

"Alkylsulfonyl" refers to an alkyl as defined herein attached through a sulfonyl bridge (i.e., —S(═O)$_2$alkyl) such as mesyl and the like, and "arylsulfonyl" refers to an aryl attached through a sulfonyl bridge (i.e., —S(═O)$_2$aryl).

"Alkylsulfamoyl" refers to an alkyl as defined herein attached through a sulfamoyl bridge (i.e., —NHS(═O)$_2$alkyl), and an "Arylsulfamoyl" refers to an alkyl attached through a sulfamoyl bridge (i.e., —NHS(═O)$_2$aryl).

"Alkylsulfinyl" refers to an alkyl as defined herein attached through a sulfinyl bridge (i.e. —S(═O)alkyl).

The terms "halogen" and "halo" refer to fluorine, chlorine, bromine, and iodine.

The term "substituted" refers to a molecule wherein at least one hydrogen atom is replaced with a substituent. When substituted, one or more of the groups are "substituents." The molecule may be multiply substituted. In the case of an oxo substituent ("═O"), two hydrogen atoms are replaced. Example substituents within this context may include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, —NR$_a$R$_b$, —NR$_a$C(═O)R$_b$, —NR$_a$C(═O)NR$_a$NR$_b$, —NR$_a$C(═O)OR$_b$, —NR$_a$SO$_2$R$_b$, —C(═O)R$_a$, —C(═O) OR$_a$, —C(═O)NR$_a$R$_b$, —OC(═O)NR$_a$R$_b$, —OR$_a$, —SR$_a$, —SOR$_a$, —S(═O)$_2$R$_a$, —OS(═O)$_2$R$_a$ and —S(═O)$_2$OR$_a$. R$_a$ and R$_b$ in this context may be the same or different and independently hydrogen, halogen hydroxyl, alkyl, alkoxy, alkyl, amino, alkylamino, dialkylamino, carbocyclyl, carbocycloalkyl, heterocarbocyclyl, heterocarbocycloalkyl, aryl, arylalkyl, heteroaryl, heteroarylalkyl.

The term "optionally substituted," as used herein, means that substitution is optional and therefore it is possible for the designated atom to be unsubstituted.

As used herein, "salts" refer to derivatives of the disclosed compounds where the parent compound is modified making acid or base salts thereof. Examples of salts include, but are not limited to, mineral or organic acid salts of basic residues such as amines, alkylamines, or dialkylamines; alkali or organic salts of acidic residues such as carboxylic acids; and the like. In preferred embodiment the salts are conventional nontoxic pharmaceutically acceptable salts including the quaternary ammonium salts of the parent compound formed, and non-toxic inorganic or organic acids. Preferred salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

"Subject" refers any animal, preferably a human patient, livestock, or domestic pet.

The term "prodrug" refers to an agent that is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis.

As used herein, the term "derivative" refers to a structurally similar compound that retains sufficient functional attributes of the identified analogue. The derivative may be structurally similar because it is lacking one or more atoms, substituted, a salt, in different hydration/oxidation states, or because one or more atoms within the molecule are switched, such as, but not limited to, replacing an oxygen atom with a sulfur or nitrogen atom or replacing an amino group with a hydroxyl group or vice versa. The derivative may be a prodrug. Derivatives may be prepare by any variety of synthetic methods or appropriate adaptations presented in synthetic or organic chemistry text books, such as those provide in March's Advanced Organic Chemistry: Reactions, Mechanisms, and Structure, Wiley, 6th Edition (2007) Michael B. Smith or Domino Reactions in Organic Synthesis, Wiley (2006) Lutz F. Tietze hereby incorporated by reference.

As used herein, the terms "prevent" and "preventing" include the prevention of the recurrence, spread or onset. It is not intended that the present disclosure be limited to complete prevention. In some embodiments, the onset is delayed, or the severity of the disease is reduced.

As used herein, the terms "treat" and "treating" are not limited to the case where the subject (e.g. patient) is cured and the disease is eradicated. Rather, embodiments, of the present disclosure also contemplate treatment that merely reduces symptoms, and/or delays disease progression.

Thieno[2,3-d]Pyrimidin-4-One and Derivatives

The disclosure relates to compounds disclosed herein, derivatives, prodrugs, esters, or salts and compositions thereof. Without meaning to be limited by theory, it is believed that these compounds are modulators of NMDA receptors.

The disclosure further relates to pharmaceutical compositions comprising thieno[2,3-d]pyrimidin-4-one derivatives of Formula I,

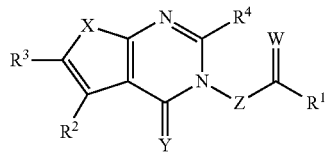

Formula I prodrugs or salts thereof wherein,

W is independently selected from S, O, NH, NR$^5$, or absent;

R$^5$ is C$_{1-4}$ alkyl, alkylaryl, aryl, heteroaryl;

X is independently selected from S, O, NH, NR$^5$;

Y is independently selected from S, O, NH, NR$^5$;

Z is independently selected from NH, CH$_2$, [C(R$^6$)$_2$]$_n$;

R$^6$ is hydrogen or an optionally substituted alkyl or heteroalkyl;

n is 1, 2 or 3;

R$^3$ is a hydrogen, a straight-chained or branched C$_{1-6}$ alkyl group, an aromatic ring, a heteroaromatic ring;

R$^2$ is a hydrogen, a substituted straight-chained or branched C$_{1-6}$ alkyl group, a substituted aromatic ring, an substituted heteroaromatic ring, a carboxy, C$_{1-3}$-alkoxycarbonyl, —CONH$_2$, —CONHR$^7$, —CONH—OR$^7$, —CONH—SO$_2$R$^7$, or —CO—NH-L-R$^8$ group, wherein L is a —(CH$_2$)$_n$;

R$^8$ is —OH, —NH$_2$, —NHR$^7$, —N(R$^7$)$_2$, —NH—COR$^7$ or a 3- to 6-membered cyclic amine such as pyrrolidine or piperidine, n is 2 or 3; and R$^7$ is C$_{1-4}$ alkyl, alkyl, alkylaryl, aryl, heteroaryl;

$R^1$ is $C_{1-4}$ alkyl, alkylaryl, aryl, heteroaryl, $CF_3$, COR', COOR', CONR'$_2$, OR', SR', SOR', SO$_2$R', NR'$_2$, NR'(CO)R', NR'C(O)OR', NR'C(O)NR'$_2$, NR'SO$_2$NR'$_2$ or NR'SO$_2$R', wherein each R' as described herein;

$R^4$ is $C_{1-4}$ alkyl, alkylaryl, aryl, heteroaryl, OR', SR', SOR', SO$_2$R', NR'$_2$, NR'(CO)R', NR'C(O)OR', NR'C(O)NR'$_2$, NR'SO2NR'$_2$ or NR'SO$_2$R', wherein each R' as described herein.

All the substituents may be optionally substituted. Typical optional substituents on alkyl, aromatic, and heteroaromatic groups may include independently halo, CN, NO$_2$, CF$_3$, OCF$_3$, COR', COOR', CONR'$_2$, OR', SR', SOR', SO$_2$R', NR'$_2$, NR'(CO)R', NR'C(O)OR', NR'C(O)NR'$_2$, NR'SO$_2$NR'$_2$ or NR'SO$_2$R', wherein each R' is independently H or an optionally substituted group selected from alkyl, alkenyl, alkynyl, heteroaryl, and aryl (all as defined herein); or the substituent maybe an optionally substituted group from alkyl, alkenyl, alkynyl, heteroalkyl, heteroalkenyl, heteroalkynyl, aryl, heteroaryl, O-aryl, O-heteroaryl, and arylalkyl.

By way of example, compounds of Formula I are those, wherein W, Y, Z, $R^1$, $R^2$, $R^3$, $R^4$ are as defined herein and X is S.

Optionally, compounds of Formula I, wherein Y, W, Z, $R^1$, are as defined herein and, $R^4$ is hydrogen.

Compounds of Formula I include those in which W, Z, $R^1$ are as defined herein and, Y is O.

Optionally, compounds of Formula I include those wherein W, $R^1$, are as defined herein and, Z is a —CH$_2$.

Optionally, compounds of Formula I include those wherein $R^1$ is as defined herein and W is O.

Optionally, compounds of Formula I include those wherein W is absent to provide a compound according to the following structure:

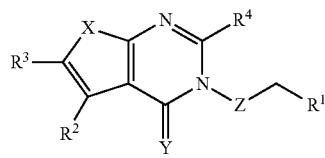

The disclosure relates to pharmaceutical compositions comprising compounds of Formula I,

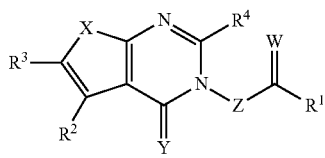

Formula I prodrugs or salts thereof wherein,
X is S, O, or NH;
Y is S, O, or NH;
Z is S, O, NH, or CH$_2$;
W is O, S, or NH;
$R^1$ is hydrogen, alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^1$ is optionally substituted with one or more, the same or different, $R^5$;

$R^2$ is alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^2$ is optionally substituted with one or more, the same or different, $R^5$;

$R^3$ is hydrogen, alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^3$ is optionally substituted with one or more, the same or different, $R^5$;

$R^4$ is hydrogen, alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^4$ is optionally substituted with one or more, the same or different, $R^5$;

$R^5$ is alkyl, halogen, nitro, cyano, hydroxy, amino, mercapto, formyl, carboxy, carbamoyl, alkoxy, alkanoyl, alkylthio, alkylamino, (alkyl)$_2$amino, alkylsulfinyl, alkylsulfonyl, arylsulfonyl, carbocyclyl, aryl, or heterocyclyl, wherein $R^5$ is optionally substituted with one or more, the same or different, $R^6$;

$R^6$ is alkyl, halogen, nitro, cyano, hydroxy, amino, mercapto, formyl, carboxy, carbamoyl, alkoxy, alkanoyl, alkylthio, alkylamino, (alkyl)$_2$amino, alkylsulfinyl, alkylsulfonyl, arylsulfonyl, carbocyclyl, aryl, or heterocyclyl, wherein $R^6$ is optionally substituted with one or more, the same or different, $R^7$; and $R^7$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

Optionally, $R^3$ is hydrogen, alkyl or methyl, $R^4$ is hydrogen, n is 1; X is S; Z is CH$_2$; and W is O.

$R^1$ is optionally a heterocyclyl or pyrrolidin-1-yl.

$R^1$ is optionally —N($R^5$)$_2$ wherein the two $R^5$ are alkyl or optionally come together to form a heterocyclyl.

$R^2$ is optionally a six-membered aryl, heteroaryl, or phenyl that is para substituted.

In certain embodiments, $R^2$ is a six-membered aryl, heteroaryl, or phenyl that is meta substituted.

$R^2$ is optionally phenyl substituted with a halogen.

Optionally, $R^1$ is a pyrrolidin-1-yl and $R^2$ is carbocyclyl, aryl, or heterocyclyl.

$R^1$ is optionally —N($R^5$)$_2$ wherein the two $R^5$ are alkyl or optionally come together to form a heterocyclyl and $R^2$ is carbocyclyl, aryl, or heterocyclyl.

$R^1$ is optionally —NHR$^5$ and $R^2$ is phenyl that is para or meta substituted.

$R^1$ is optionally —NHR$^5$ and $R^2$ is phenyl substituted with a halogen.

$R^1$ is optionally —NHR$^5$ and $R^2$ is phenyl that is para or meta substituted with a halogen.

The disclosure further relates to compound of Formula IA

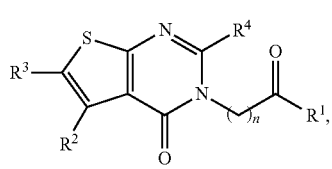

Formula IA prodrugs or salts thereof wherein, n is 1 or 2;

$R^1$ is hydrogen, alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^1$ is optionally substituted with one or more, the same or different, $R^5$;

$R^2$ is alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^2$ is optionally substituted with one or more, the same or different, $R^5$;

$R^3$ is hydrogen, alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^3$ is optionally substituted with one or more, the same or different, $R^5$;

$R^4$ is hydrogen, alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^4$ is optionally substituted with one or more, the same or different, $R^5$;

$R^5$ is alkyl, halogen, nitro, cyano, hydroxy, amino, mercapto, formyl, carboxy, carbamoyl, alkoxy, alkanoyl, alkylthio, alkylamino, (alkyl)$_2$amino, alkylsulfinyl, alkylsulfonyl, arylsulfonyl, carbocyclyl, aryl, or heterocyclyl, wherein $R^5$ is optionally substituted with one or more, the same or different, $R^6$;

$R^6$ is alkyl, halogen, nitro, cyano, hydroxy, amino, mercapto, formyl, carboxy, carbamoyl, alkoxy, alkanoyl, alkylthio, alkylamino, (alkyl)$_2$amino, alkylsulfinyl, alkylsulfonyl, arylsulfonyl, carbocyclyl, aryl, or heterocyclyl, wherein $R^6$ is optionally substituted with one or more, the same or different, $R^7$; and $R^7$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

The disclosure relates to the compound of Formula IB

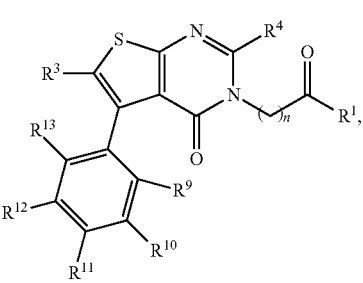

Formula IB prodrugs or salts thereof wherein, n is 1 or 2;

$R^1$ is hydrogen, alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^1$ is optionally substituted with one or more, the same or different, $R^5$;

$R^3$ is hydrogen, alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^3$ is optionally substituted with one or more, the same or different, $R^5$;

$R^4$ is hydrogen, alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^4$ is optionally substituted with one or more, the same or different, $R^5$;

$R^5$ is alkyl, halogen, nitro, cyano, hydroxy, amino, mercapto, formyl, carboxy, carbamoyl, alkoxy, alkanoyl, alkylthio, alkylamino, (alkyl)$_2$amino, alkylsulfinyl, alkylsulfonyl, arylsulfonyl, carbocyclyl, aryl, or heterocyclyl, wherein $R^5$ is optionally substituted with one or more, the same or different, $R^6$;

$R^6$ is alkyl, halogen, nitro, cyano, hydroxy, amino, mercapto, formyl, carboxy, carbamoyl, alkoxy, alkanoyl, alkylthio, alkylamino, (alkyl)$_2$amino, alkylsulfinyl, alkylsulfonyl, arylsulfonyl, carbocyclyl, aryl, or heterocyclyl, wherein $R^6$ is optionally substituted with one or more, the same or different, $R^7$;

$R^7$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$R^9$, $R^{10}$, $R^{11}$, $R^{12}$, and $R^{13}$, are each individually and independently selected from hydrogen, alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R_9$, $R^{10}$, $R^{11}$, $R^{12}$, and $R^{13}$, are optionally substituted with one or more, the same or different, $R^{15}$;

$R^{15}$ is alkyl, halogen, nitro, cyano, hydroxy, amino, mercapto, formyl, carboxy, carbamoyl, alkoxy, alkanoyl, alkylthio, alkylamino, (alkyl)$_2$amino, alkylsulfinyl, alkylsulfonyl, arylsulfonyl, carbocyclyl, aryl, or heterocyclyl, wherein $R^{15}$ is optionally substituted with one or more, the same or different, $R^{16}$;

$R^{16}$ is alkyl, halogen, nitro, cyano, hydroxy, amino, mercapto, formyl, carboxy, carbamoyl, alkoxy, alkanoyl, alkylthio, alkylamino, (alkyl)$_2$amino, alkylsulfinyl, alkylsulfonyl, arylsulfonyl, carbocyclyl, aryl, or heterocyclyl, wherein $R^{16}$ is optionally substituted with one or more, the same or different, $R^{17}$; and $R^{17}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

Optionally, $R^1$ is a heterocyclyl or a five membered heterocyclyl.
Optionally, $R^{10}$ is halogen.
Optionally, $R^{11}$ is halogen.
Optionally, $R^9$ is hydrogen.
Optionally, $R^{10}$ is hydrogen.
Optionally, $R^{13}$ is hydrogen.
Optionally, $R^{12}$ is hydrogen.

The disclosure also relates to compound of Formula IC

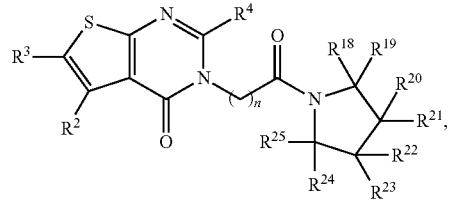

Formula IC prodrugs or salts thereof wherein,
n is 1 or 2;
$R^2$ is alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^2$ is optionally substituted with one or more, the same or different, $R^5$;

$R^3$ is hydrogen, alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^3$ is optionally substituted with one or more, the same or different, $R^5$;

$R^4$ is hydrogen, alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^4$ is optionally substituted with one or more, the same or different, $R^5$;

$R^5$ is alkyl, halogen, nitro, cyano, hydroxy, amino, mercapto, formyl, carboxy, carbamoyl, alkoxy, alkanoyl, alkylthio, alkylamino, (alkyl)$_2$amino, alkylsulfinyl, alkylsulfonyl, arylsulfonyl, carbocyclyl, aryl, or heterocyclyl, wherein $R^5$ is optionally substituted with one or more, the same or different, $R^6$;

$R^6$ is alkyl, halogen, nitro, cyano, hydroxy, amino, mercapto, formyl, carboxy, carbamoyl, alkoxy, alkanoyl, alkylthio, alkylamino, (alkyl)$_2$amino, alkylsulfinyl, alkylsulfonyl, arylsulfonyl, carbocyclyl, aryl, or heterocyclyl, wherein $R^6$ is optionally substituted with one or more, the same or different, $R^7$; and $R^7$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$R^{18}$, $R^{19}$, $R^{20}$, $R^{21}$, $R^{22}$, $R^{23}$, $R^{24}$, and $R^{25}$, are each individual) and independently selected from hydrogen, alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^{18}$, $R^{19}$, $R^{20}$, $R^{21}$, $R^{22}$, $R^{23}$, $R^{24}$, and $R^{25}$, are optionally substituted with one or more, the same or different, $R^{26}$;

$R^{26}$ is alkyl, halogen, nitro, cyano, hydroxy, amino, mercapto, formyl, carboxy, carbamoyl, alkoxy, alkanoyl, alkylthio, alkylamino, (alkyl)$_2$amino, alkylsulfinyl, alkylsulfonyl, arylsulfonyl, carbocyclyl, aryl, or heterocyclyl, wherein $R^{26}$ is optionally substituted with one or more, the same or different, $R^{27}$;

$R^{27}$ is alkyl, halogen, nitro, cyano, hydroxy, amino, mercapto, formyl, carboxy, carbamoyl, alkoxy, alkanoyl, alkylthio, alkylamino, (alkyl)$_2$amino, alkylsulfinyl, alkylsulfonyl, arylsulfonyl, carbocyclyl, aryl, or heterocyclyl, wherein $R^{27}$ is optionally substituted with one or more, the same or different, $R^{28}$; and $R^{28}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

Optionally, $R^2$ is aryl, phenyl, or heterocyclyl optionally substituted.

The disclosure further relates to compound of Formula ID

Formula ID

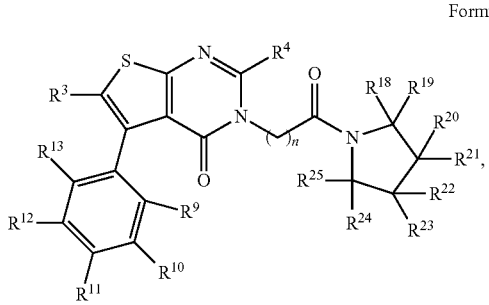

prodrugs or salts thereof wherein, n is 1 or 2;

$R^3$ is hydrogen, alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^3$ is optionally substituted with one or more, the same or different, $R^5$;

$R^4$ is hydrogen, alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^4$ is optionally substituted with one or more, the same or different, $R^5$;

$R^5$ is alkyl, halogen, nitro, cyano, hydroxy, amino, mercapto, formyl, carboxy, carbamoyl, alkoxy, alkanoyl, alkylthio, alkylamino, (alkyl)$_2$amino, alkylsulfinyl, alkylsulfonyl, arylsulfonyl, carbocyclyl, aryl, or heterocyclyl, wherein $R^5$ is optionally substituted with one or more, the same or different, $R^6$;

$R^6$ is alkyl, halogen, nitro, cyano, hydroxy, amino, mercapto, formyl, carboxy, carbamoyl, alkoxy, alkanoyl, alkylthio, alkylamino, (alkyl)$_2$amino, alkylsulfinyl, alkylsulfonyl, arylsulfonyl, carbocyclyl, aryl, or heterocyclyl, wherein $R^6$ is optionally substituted with one or more, the same or different, $R^7$; and $R^7$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$R^9$, $R^{10}$, $R^{11}$, $R^{12}$, and $R^{13}$, are each individually and independently selected from hydrogen, alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^9$, $R^{10}$, $R^{11}$, $R^{12}$, and $R^{13}$, are optionally substituted with one or more, the same or different, $R^{15}$;

$R^{15}$ is alkyl, halogen, nitro, cyano, hydroxy, amino, mercapto, formyl, carboxy, carbamoyl, alkoxy, alkanoyl, alkylthio, alkylamino, (alkyl)$_2$amino, alkylsulfinyl, alkylsulfonyl, arylsulfonyl, carbocyclyl, aryl, or heterocyclyl, wherein $R^{15}$ is optionally substituted with one or more, the same or different, $R^{16}$;

$R^{16}$ is alkyl, halogen, nitro, cyano, hydroxy, amino, mercapto, formyl, carboxy, carbamoyl, alkoxy, alkanoyl, alkylthio, alkylamino, (alkyl)$_2$amino, alkylsulfinyl, alkylsulfonyl, arylsulfonyl, carbocyclyl, aryl, or heterocyclyl, wherein $R^{16}$ is optionally substituted with one or more, the same or different, $R^{17}$;

$R^{17}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$R^{18}$, $R^{19}$, $R^{20}$, $R^{21}$, $R^{22}$, $R^{23}$, $R^{24}$, and $R^{25}$, are each individual) and independently selected from hydrogen, alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^{18}$, $R^{19}$, $R^{20}$, $R^{21}$, $R^{22}$, $R^{23}$, $R^{24}$, and $R^{25}$, are optionally substituted with one or more, the same or different, $R^{26}$;

$R^{26}$ is alkyl, halogen, nitro, cyano, hydroxy, amino, mercapto, formyl, carboxy, carbamoyl, alkoxy, alkanoyl, alkylthio, alkylamino, (alkyl)$_2$amino, alkylsulfinyl, alkylsulfonyl, arylsulfonyl, carbocyclyl, aryl, or heterocyclyl, wherein $R^{26}$ is optionally substituted with one or more, the same or different, $R^{27}$;

$R^{27}$ is alkyl, halogen, nitro, cyano, hydroxy, amino, mercapto, formyl, carboxy, carbamoyl, alkoxy, alkanoyl, alkylthio, alkylamino, (alkyl)$_2$amino, alkylsulfinyl, alkylsulfonyl, arylsulfonyl, carbocyclyl, aryl, or heterocyclyl, wherein $R^{27}$ is optionally substituted with one or more, the same or different, $R^{28}$; and $R^{28}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

The disclosure further relates to compound of Formula IE

Formula IE

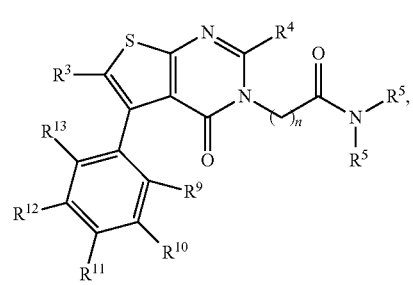

prodrugs or salts thereof wherein, n is 1 or 2;

$R^1$ is hydrogen, alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^1$ is optionally substituted with one or more, the same or different, $R^5$;

$R^3$ is hydrogen, alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^3$ is optionally substituted with one or more, the same or different, $R^5$;

$R^4$ is hydrogen, alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^4$ is optionally substituted with one or more, the same or different, $R^5$;

$R^5$ is as each occurrence individually and independently alkyl, halogen, nitro, cyano, hydroxy, amino, mercapto, formyl, carboxy, carbamoyl, alkoxy, alkanoyl, alkylthio, alkylamino, (alkyl)$_2$amino, alkylsulfinyl, alkylsulfonyl, arylsulfonyl, carbocyclyl, aryl, or heterocyclyl, wherein $R^5$ is optionally substituted with one or more, the same or different, $R^6$; or two $R^5$ come together to form a heterocyclic ring;

$R^6$ is alkyl, halogen, nitro, cyano, hydroxy, amino, mercapto, formyl, carboxy, carbamoyl, alkoxy, alkanoyl, alkylthio, alkylamino, (alkyl)$_2$amino, alkylsulfinyl, alkylsulfonyl, arylsulfonyl, carbocyclyl, aryl, or heterocyclyl, wherein $R^6$ is optionally substituted with one or more, the same or different, $R^7$;

$R^7$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$R^9$, $R^{10}$, $R^{11}$, $R^{12}$, and $R^{13}$, are each individually and independently selected from hydrogen, alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^9$, $R^{10}$, $R^{11}$, $R^{12}$, and $R^{13}$, are optionally substituted with one or more, the same or different, $R^{15}$;

$R^{15}$ is alkyl, halogen, nitro, cyano, hydroxy, amino, mercapto, formyl, carboxy, carbamoyl, alkoxy, alkanoyl, alkylthio, alkylamino, (alkyl)$_2$amino, alkylsulfinyl, alkylsulfonyl, arylsulfonyl, carbocyclyl, aryl, or heterocyclyl, wherein $R^{15}$ is optionally substituted with one or more, the same or different, $R^{16}$;

$R^{16}$ is alkyl, halogen, nitro, cyano, hydroxy, amino, mercapto, formyl, carboxy, carbamoyl, alkoxy, alkanoyl, alkylthio, alkylamino, (alkyl)$_2$amino, alkylsulfinyl, alkylsulfonyl, arylsulfonyl, carbocyclyl, aryl, or heterocyclyl, wherein $R^{16}$ is optionally substituted with one or more, the same or different, $R^{17}$; and $R^{17}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

The disclosure further relates to pharmaceutical compositions comprising compounds according to Formula II,

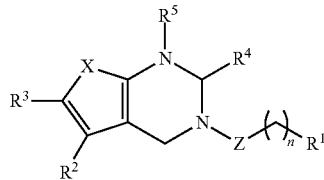

Formula II prodrugs or salts thereof wherein, n is 0, 1, 2, 3, 4, or 5;

$R^1$ is hydrogen, alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^1$ is optionally substituted with one or more, the same or different, $R^5$;

$R^2$ is alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^2$ is optionally substituted with one or more, the same or different, $R^5$;

$R^3$ is hydrogen, alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^3$ is optionally substituted with one or more, the same or different, $R^5$;

$R^4$ is hydrogen, alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^4$ is optionally substituted with one or more, the same or different, $R^5$;

$R^5$ is alkyl, halogen, nitro, cyano, hydroxy, amino, mercapto, formyl, carboxy, carbamoyl, alkoxy, alkanoyl, alkylthio, alkylamino, (alkyl)$_2$amino, alkylsulfinyl, alkylsulfonyl, arylsulfonyl, carbocyclyl, aryl, or heterocyclyl, wherein $R^5$ is optionally substituted with one or more, the same or different, $R^6$;

$R^6$ is alkyl, halogen, nitro, cyano, hydroxy, amino, mercapto, formyl, carboxy, carbamoyl, alkoxy, alkanoyl, alkylthio, alkylamino, (alkyl)$_2$amino, alkylsulfinyl, alkylsulfonyl, arylsulfonyl, carbocyclyl, aryl, or heterocyclyl, wherein $R^6$ is optionally substituted with one or more, the same or different, $R^7$; and $R^7$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

X is independently selected from S, O, NH, $NR^5$; and

Z is independently selected from NH, $CH_2$, $[C(R^6)_2]_m$, wherein m is 1, 2, or 3.

All the substituents in Formula II may be optionally substituted. Typical optional substituents on alkyl, aromatic, and heteroaromatic groups may include independently halo, CN, $NO_2$, $CF_3$, $OCF_3$, COR', COOR', $CONR'_2$, OR', SR', SOR', $SO_2R'$, $NR'_2$, NR'(CO)R', NR'C(O)OR', $NR'C(O)NR'_2$, $NR'SO_2NR'_2$ or $NR'SO_2R'$, wherein each R' is independently H or an optionally substituted group selected from alkyl, alkenyl, alkynyl, heteroaryl, and aryl (all as defined herein); or the substituent maybe an optionally substituted group from alkyl, alkenyl, alkynyl, heteroalkyl, heteroalkenyl, heteroalkynyl, aryl, heteroaryl, O-aryl, O-heteroaryl, and arylalkyl.

By way of example, compounds of Formula II are those, wherein n, Z, $R^1$, $R^2$, $R^3$, $R^4$, and $R^5$ are as defined herein and X is S.

Optionally, $R^2$ and $R^3$ are methyl.

Optionally, $R^4$ is hydrogen.

Optionally, Z is $CH_2$.

The disclosure further relates to compound of Formula IIA

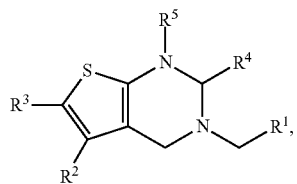

Formula IIA prodrugs or salts thereof wherein, $R^1$ is $C_{1-4}$ alkyl, alkylaryl, aryl, heteroaryl, $CF_3$, COR', COOR', $CONR'_2$, OR', SR', SOR', $SO_2R'$, $NR'_2$, NR'(CO)R', NR'C(O)OR', $NR'C(O)NR'_2$, $NR'SO_2NR'_2$ or $NR'SO_2R'$, wherein each R' is as described herein;

$R^2$ is a hydrogen, a substituted straight-chained or branched $C_{1-6}$ alkyl group, a substituted aromatic ring, an substituted heteroaromatic ring, a carboxy, $C_{1-3}$-alkoxycarbonyl, $-CONH_2$, $-CONHR^7$, $-CONH-OR^7$, $-CONH-SO_2R^7$, or $-CO-NH-L-R^8$ group, wherein L is a $-(CH_2)_n$;

$R^3$ is a hydrogen, a straight-chained or branched $C_{1-6}$ alkyl group, an aromatic ring, a heteroaromatic ring;

$R^4$ is $C_{1-4}$ alkyl, alkylaryl, aryl, heteroaryl, OR', SR', SOR', $SO_2R'$, $NR'_2$, NR'(CO)R', NR'C(O)OR', $NR'C(O)NR'_2$, $NR'SO2NR'_2$ or $NR'SO_2R'$, wherein each R' as described herein;

$R^5$ is $C_{1-4}$ alkyl, alkylaryl, aryl, or heteroaryl;

$R^7$ is $C_{1-4}$ alkyl, alkyl, alkylaryl, aryl, heteroaryl; and $R^8$ is $-OH$, $-NH_2$, $-NHR^7$, $-N(R^7)_2$, $-NH-COR'$ or a 3- to 6-membered cyclic amine such as pyrrolidine or piperidine.

The disclosure further relates to compound of Formula IIB

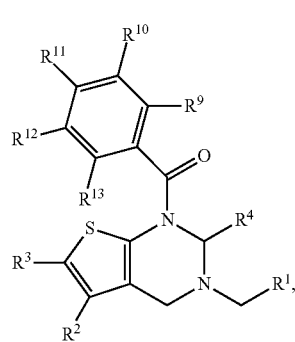

Formula IIB prodrugs or salts thereof wherein, $R^1$ is $C_{1-4}$ alkyl, alkylaryl, aryl, heteroaryl, $CF_3$, COR', COOR', $CONR'_2$, OR', SR', SOR', $SO_2R'$, $NR'_2$, NR'(CO)R', NR'C(O)OR', $NR'C(O)NR'_2$, $NR'SO_2NR'_2$ or $NR'SO_2R'$, wherein each R' is as described herein;

$R^2$ is a hydrogen, a substituted straight-chained or branched $C_{1-6}$ alkyl group, a substituted aromatic ring, an substituted heteroaromatic ring, a carboxy, $C_{1-3}$-alkoxycarbonyl, $-CONH_2$, $-CONHR^7$, $-CONH-OR^7$, $-CONH-SO_2R^7$, or $-CO-NH-L-R^8$ group, wherein L is a $-(CH_2)_n$;

$R^3$ is a hydrogen, a straight-chained or branched $C_{1-6}$ alkyl group, an aromatic ring, a heteroaromatic ring;

$R^4$ is $C_{1-4}$ alkyl, alkylaryl, aryl, heteroaryl, OR', SR', SOR', $SO_2R'$, $NR'_2$, NR'(CO)R', NR'C(O)OR', $NR'C(O)NR'_2$, $NR'SO2NR'_2$ or $NR'SO_2R'$, wherein each R' as described herein;

$R^7$ is $C_{1-4}$ alkyl, alkyl, alkylaryl, aryl, heteroaryl;

$R^8$ is $-OH$, $-NH_2$, $-NHR^7$, $-N(R^7)_2$, $-NH-COR'$ or a 3- to 6-membered cyclic amine such as pyrrolidine or piperidine; and $R^9$, $R^{10}$, $R^{11}$, $R^{12}$, and $R^{13}$, are each individually and independently selected from hydrogen, alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^9$, $R^{10}$, $R^{11}$, $R^{12}$, and $R^{13}$, are optionally substituted with one or more, the same or different, R'.

Methods of Synthesis

The compounds described herein can be prepared in a variety of ways. The compounds can be synthesized using various synthetic methods. At least some of these methods are known in the art of synthetic organic chemistry. The compounds described herein can be prepared from readily available starting materials. Optimum reaction conditions can vary with the particular reactants or solvent used, but such conditions can be determined by one skilled in the art by routine optimization procedures.

Variations on Formula I and Formula II include the addition, subtraction, or movement of the various constituents as described for each compound. Similarly, when one or more chiral centers are present in a molecule, all possible chiral variants are included. Additionally, compound synthesis can involve the protection and deprotection of various chemical groups. The use of protection and deprotection and the selection of appropriate protecting groups can be determined by one skilled in the art. The chemistry of protecting groups can be found, for example, in Wuts, Greene's Protective Groups in Organic Synthesis, 5th. Ed., Wiley & Sons, 2014, which is incorporated herein by reference in its entirety.

Reactions to produce the compounds described herein can be carried out in solvents, which can be selected by one of skill in the art of organic synthesis. Solvents can be substantially nonreactive with the starting materials (reactants), the intermediates, or products under the conditions at which the reactions are carried out, i.e., temperature and pressure. Reactions can be carried out in one solvent or a mixture of more than one solvent. Product or intermediate formation can be monitored according to any suitable method known in the art. For example, product formation can be monitored by spectroscopic means, such as nuclear magnetic resonance spectroscopy (e.g., $^1$H or $^{13}$C) infrared spectroscopy, spectrophotometry (e.g., UV-visible), or mass spectrometry, or by chromatography such as high performance liquid chromatography (HPLC) or thin layer chromatography.

Compounds described by Formula I and pharmaceutically acceptable salts thereof can be made using the methods shown in Scheme 1, which depicts the synthesis of compounds of Formula IA wherein n is 1.

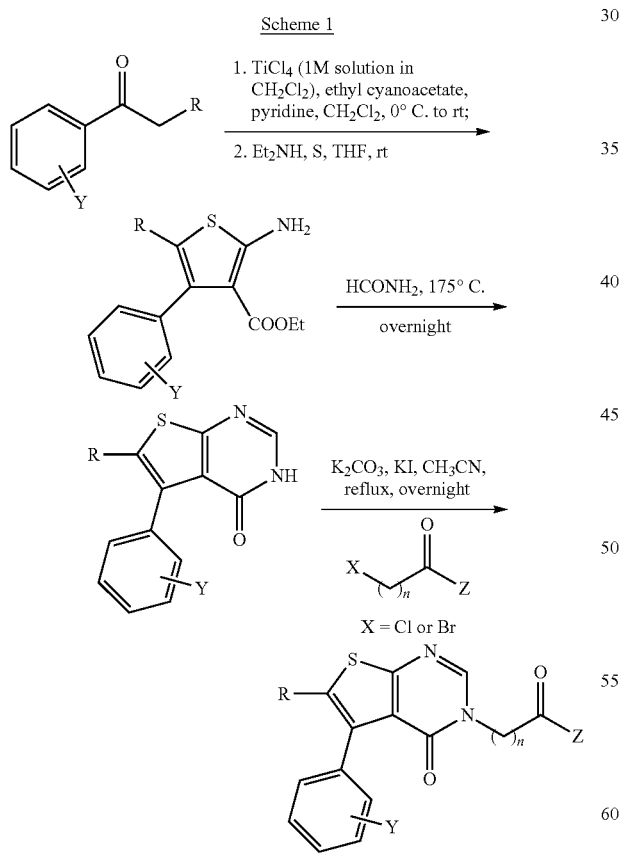

Compounds described by Formula I and pharmaceutically acceptable salts thereof can be made using the methods shown in Scheme 2, which depicts the synthesis of compounds of Formula IA wherein n is 1.

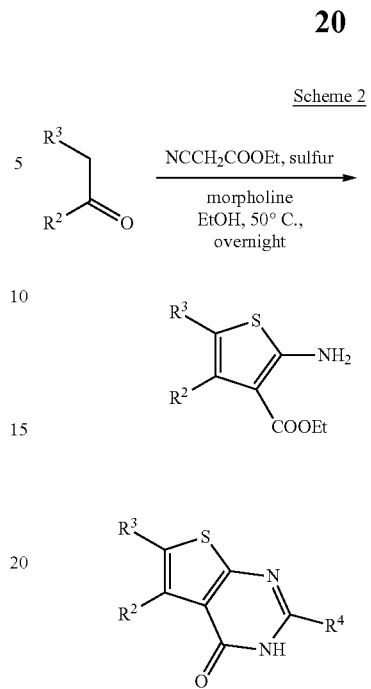

Compounds described by Formula I and pharmaceutically acceptable salts thereof can be made using the methods shown in Scheme 3, which depicts the synthesis of compounds of Formula IE wherein n is 1 and $R^2$ is an optionally substituted phenyl.

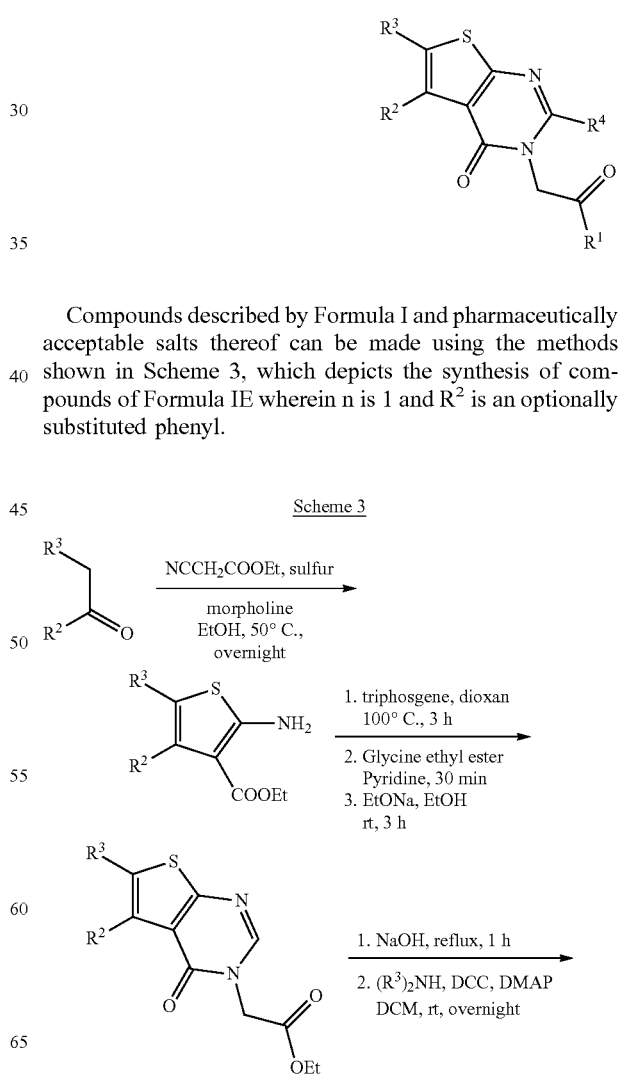

-continued

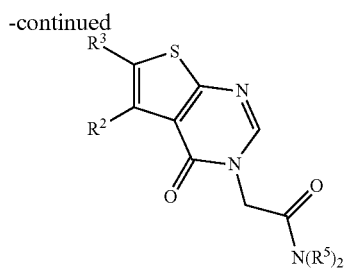

Detailed methods for synthesizing the compounds described herein are provided in the Examples section below.

Methods of Use

The compounds described herein can generally be used to treat, prevent or produce a reduction in symptoms of neurologic disorders, which includes abnormalities of the nervous system. These disorders can be characterized by primary location, dysfunction/abnormality or cause. Central nervous system disorders impact the brain or spinal cord, while peripheral nervous system disorders affect the nerves. Causes include, for example, genetic abnormalities, developmental abnormalities, injury, ischemia, or trauma, infection, cancer or diseases and disorders of the vasculature that supplies the nervous system, for example stroke. In certain instances, the neurologic disorder may be associated with NMDA receptor activation, and in particular with activation of NMDA receptors including a GluN2B subunit.

Disorders that can be treated, prevented or for which symptoms can be reduced include neuropsychiatric disorders, neurodegenerative disorders, as well as neurologic disorders including neuropathic pain, inflammatory pain, stroke, traumatic brain injury, epilepsy, transient ischemia, global ischemia, hypoxia, spinal cord trauma and other neurologic events.

Optionally, the compounds are used for the treatment or prevention of neuropsychiatric disorders. These disorders include, without limitation, depression, anxiety, bipolar disorder, obsessive-compulsive disorder, alcohol and substance abuse, and attention-deficit hyperactivity disorder.

The compounds are optionally used for the treatment or prevention of neurodegenerative disorders. These disorders are typically characterized by gradual and progressive nervous system dysfunction due to loss of neuronal cells and neuronal tissue and include, without limitation, Alzheimer's disease, Parkinson's disease, Huntington's disease, Amyotrophic lateral sclerosis (ALS/Lou Gehrig's disease), Multiple Sclerosis, spinal muscular atrophy, spinal & bulbar muscular atrophy, familial spastic paraparesis, Machado Joseph disease Friedreich's ataxia and Lewy body disease.

Methods of treatment of a neurologic disorder are provided. The method includes administering a compound of Formula I, or a pharmaceutically acceptable salt, ester or prodrug thereof, to a host in need thereof. By way of example, the disorder is associated with NMDA receptor activation. The disorder is optionally a neuropsychiatric disorder, a neurodegenerative disorder, neuropathic pain. The disorder is optionally an injury resulting from an ischemic event or neuropathic injury or infection.

Provided herein are methods to prevent neurodegeneration in patients with Parkinson's, Alzheimer's, Huntington's chorea, ALS, and other neurodegenerative conditions.

Uses of the compounds in the treatment or manufacture of a medicament for such disorders are also provided.

Provided herein is a method of treatment or prevention of neurologic disorder, such as a neuropsychiatric or neurodegenerative disease or disorder or a disorder resulting from injury, trauma, infection or ischemia, in a host, including administering a compound of Formula I or a pharmaceutically acceptable salt, ester or prodrug thereof to the host, either alone or in combination, in which the host is suffering from a reduced pH in a region of the brain. By way of example, the disorder has caused a region with a pH below pH 7.6, or below 7.5, or below 7.4, or below 7.3, or below 7.2, or below 7.1, or below 7, or below 6.9, or below 6.8, or below 6.7, or below 6.6 or below 6.5 or below 6.4. Optionally, the reduced pH is due to pathological conditions such as hypoxia resulting from stroke, traumatic brain injury, global ischemia, such as global ischemia that may occur during cardiac surgery, hypoxia, including hypoxia that may occur following cessation of breathing, pre-eclampsia, spinal cord trauma, epilepsy, status epilepticus, neuropathic pain, inflammatory pain, chronic pain, vascular dementia and glioma tumors.

Methods are provided to attenuate the progression of an ischemic or excitotoxic cascade by administering a compound of Formula I. In addition, methods are provided to decrease infarct volume by administering a compound of Formula I. Still further, methods are provided to decrease behavioral deficits associated with an ischemic event by administering a compound of Formula I. Further, methods are provided to treat patients with ischemic injury or hypoxia, or prevent or treat the neuronal toxicity associated with ischemic injury or hypoxia, by administering a compound or composition described herein. Optionally, the ischemic injury is stroke. The ischemic injury is optionally vasospasm after subarachnoid hemorrhage. In other embodiments, the ischemic injury is selected from, but not limited to, one of the following: traumatic brain injury, cognitive deficit after bypass surgery, cognitive deficit after carotid angioplasty; and/or neonatal ischemia following hypothermic circulatory arrest.

Further, compounds selected according to the methods or processes described herein can be used prophylactically to prevent or protect against such neurologic or neuropathologic diseases, disorders or conditions, such as those described herein. Patients with a predisposition for an ischemic event, such as a genetic predisposition, can be treated prophylactically with the methods and compounds described herein. Patients at risk for or exhibiting vasospasms can be treated prophylactically with the methods and compounds described herein. Patients undergoing cardiac bypass surgery can be treated prophylactically with the methods and compounds described herein. The compounds of the present disclosure optionally is used as neuroprotectants.

Methods are provided to treat patients with neuropathic pain or related disorders by administering a compound or composition described herein. In certain embodiments, the neuropathic pain or related disorder can be selected from the group including, but not limited to: peripheral diabetic neuropathy, postherpetic neuralgia, complex regional pain syndromes, peripheral neuropathies, chemotherapy-induced neuropathic pain, cancer neuropathic pain, neuropathic low back pain, HIV neuropathic pain, trigeminal neuralgia, and/or central post-stroke pain. This dysfunction can be associated with common symptoms such as allodynia, hyperalgesia, intermittent abnormal sensations, and spontaneous, burning, shooting, stabbing, paroxysmal or electrical-sensations, paresthesias, hyperpathia and/or dysesthesias, which can also be treated by the compounds and methods described herein.

Further, the compounds and methods described herein can be used to treat neuropathic pain resulting from peripheral or central nervous system pathologic events, including, but not limited to trauma; ischemia; infections or endocrinologic disorders, including, but not limited to, diabetes mellitus, diabetic neuropathy, amyloidosis, amyloid polyneuropathy (primary and familial), neuropathies with monoclonal proteins, vasculitic neuropathy, HIV infection, herpes zoster—shingles and/or postherpetic neuralgia; neuropathy associated with Guillain-Barre syndrome; neuropathy associated with Fabry's disease; entrapment due to anatomic abnormalities; trigeminal and other CNS neuralgias; malignancies; inflammatory conditions or autoimmune disorders, including, but not limited to, demyelinating inflammatory disorders, rheumatoid arthritis, systemic lupus erythematosus, Sjogren's syndrome; and cryptogenic causes, including, but not limited to idiopathic distal small-fiber neuropathy. Other causes of neuropathic pain that can be treated according to the methods and compositions described herein include, but are not limited to, exposure to toxins or drugs (such as arsenic, thallium, alcohol, vincristine, cisplatinum and dideoxynucleosides), dietary or absorption abnormalities, immuno-globulinemias, hereditary abnormalities and amputations (including mastectomy). Neuropathic pain can also result from compression of nerve fibers, such as radiculopathies and carpal tunnel syndrome.

Methods are provided to treat patients with neurodegenerative diseases by administering a compound selected according to the methods or processes described herein. These neurodegenerative disorders include, without limitation, Alzheimer's disease, Parkinson's disease, Huntington's disease, Amyotrophic lateral sclerosis (ALS/Lou Gehrig's disease), Multiple Sclerosis, spinal muscular atrophy, spinal and bulbar muscular atrophy, familial spastic paraparesis, Machado Joseph disease, Friedreich's ataxia and Lewy body disease. For example, the neurodegenerative disease can be Parkinson's disease. Optionally, the neurodegenerative disease is Alzheimer's disease. By way of another example, the neurodegenerative disease can be Huntington's disease and/or ALS.

Further provided are methods to treat patients with brain tumors by administering a compound selected according to the methods or processes described herein. The compounds are useful in the treatment of tumor growth. For example, the compounds reduce tumor mass. The compounds are also useful in the treatment or prophylaxis of a neurologic event involving acidification of brain or spinal cord tissue. The NMDA receptor antagonists of this disclosure are useful both in the treatment of stroke and head trauma, and for use as prophylactic agents for at risk patients. The acid generated by ischemic tissue during stroke is harnessed since the neuroprotective agents described herein are more potent at acidic pH. In this way side effects are minimized in unaffected tissue since drug at these sites are less potent. These compounds may be used to reduce the amount of neuronal death associated with stroke and head trauma. They may be given chronically to individuals with epilepsy or who are at risk for stroke or head trauma, preoperatively in high risk heart/brain surgery, etc., in order to lengthen the window of opportunity for subsequent therapy.

In addition, methods are provided to treat the following diseases or neurological conditions, including, but not limited to: chronic nerve injury, chronic pain syndromes, such as, but not limited to diabetic neuropathy, ischemia, ischemia following transient or permanent vessel occlusion, seizures, spreading depression, restless leg syndrome, hypocapnia, hypercapnia, diabetic ketoacidosis, fetal asphyxia, spinal cord injury, traumatic brain injury, status epilepticus, epilepsy, hypoxia, perinatal hypoxia, concussion, migraine, hypocapnia, hyperventilation, lactic acidosis, fetal asphyxia during parturition, brain gliomas, and/or retinopathies by administering a compound selected according to the methods or processes described herein.

The compounds are used for the treatment or prevention of neuropsychiatric disorders. Generally, these disorders are mental disturbances attributable to diseases of the nervous system. These disorders include depression, anxiety, bipolar disorder, obsessive-compulsive disorder, alcohol and substance abuse, and attention-deficit hyperactivity disorder. In particular embodiments, the disorders are neuropsychiatric mood disorders, non-limiting examples of which include depression, including major depression, treatment-resistant depression and treatment-resistant bipolar depression, bipolar disorders including cyclothymia (a mild form of bipolar disorder), affective disorders such as SAD (seasonal affective disorder) and mania (euphoric, hyperactive, over inflated ego, unrealistic optimism). In certain embodiments, the disorder is treatment-resistant depression or treatment-resistant bipolar depression. Neuropsychiatric disorders also include attention deficit disorders such as ADD or ADHD. In certain embodiments, a method of treatment a neuropsychiatric disorder is provided including administering a compound of the disclosure, alone or in combination to a host diagnosed with the disorder. Uses of the compounds in the treatment or manufacture of a medicament for such disorders are also provided.

The compounds are used for the treatment of depression in a host diagnosed with the disorder. The compounds are optionally used for treatment of a bipolar disorder in a host diagnosed with the disorder. The compounds can also be used to diminish the severity of depressive or manic episodes or prevent future episodes. Further provided herein are methods of treating seasonal disorders including administering the compound to a host at risk of suffering from a SAD. In particular, the compounds can be provided on a seasonal basis. Optionally, the host has been diagnosed as suffering from or is at risk for SAD or depression. For example, the host is at risk of suffering from a mania. The mania can be characterized by euphoria, hyperactivity, over-inflated ego, or unrealistic optimism. Optionally, the host is suffering from an attention deficit disorders, for example ADD or ADHD.

Depression, formally called major depression, major depressive disorder or clinical depression, is a medical illness that involves the mind and body. Most health professionals today consider depression a chronic illness that requires long-term treatment, much like diabetes or high blood pressure. Although some people experience only one episode of depression, most have repeated episodes of depression symptoms throughout their life. Depression is also a common feature of mental illness, whatever its nature and origin. In other instances, the host does not have a history of a major psychiatric disorder but has been diagnosed with suffering from at least one depressive episode. In other instances, the host has been diagnosed with bipolar disorder. The host may also have been diagnosed as suffering from panic attacks or anxiety.

In some instances, the host is not suffering from a chronic disorder but is at risk of a depressive episode, anxiety or a panic attack due to environmental circumstances. The compounds may be given prophylactically to prevent onset of such an episode. For instance, the compounds can be provided to a host before a plane trip, a public speech, or other potential stressful even that could lead to an episode. In some embodiments, therefore, a method of prevention of a neuropsychiatric episode is provided, including administering a compound of the disclosure to a host at risk of suffering from such an episode. In some instances, the compounds are useful for treatment or prophylaxis of disorders such as depression or bipolar disorder associated with an injury or with aging.

Optionally, the compounds provided herein block the GluN2B-containing NMDA receptors, have varying activity against receptors containing GluN2A or GluN2D, and may be selective for other members of the NMDA receptor family (GluN2C, GluN3A and GluN3B). The compounds are optionally selective NMDA receptor negative modulators, blockers, or antagonists. By way of example, the compounds are NMDA receptor antagonists selective for GluN2B, GluN2A, GluN2C, GluN2D, GluN3A, and/or GluN3B that do not interact with other receptors or ion channels at therapeutic concentrations. The compound is optionally a selective GluN1/GluN2A NMDA receptor. Optionally, the compound is a selective GluN1/GluN2B NMDA receptor antagonist. By way of example, the compounds can bind to the GluN2B subunit of the NMDA receptor. Optionally, the compounds are selective for the GluN2B subunit of the NMDA receptor. The compound optionally is not an NMDA receptor glutamate site competitive antagonist. Optionally, the compound is not an NMDA receptor glycine site competitive antagonist. The compounds can optionally alter the potency of glutamate or glycine through an allosteric mechanism.

GluN2B-containing NMDA receptors may also be referred to as NR2B-containing NMDA receptors. Similarly, GluN2A is used interchangeably with NR2A, GluN2D with NR2D, GluN2C with NR2C, GluN3A with NR3A, and GluN3B with NR3B.

Optionally, the compounds are administered to a host suffering from or at risk of suffering from age-related depression. The compounds can be administered prophylactically to a host over the age of 60, or over the age of 70, or over the age of 80 to prevent or reduce the severity of depressive episodes.

Compounds of the present disclosure can be used to activate or stimulate the mTOR signaling pathway. The compounds can be used to modulate mTOR activity in the brain, for example, in the prefrontal cortex. Compounds that modulate or stimulate mTOR signaling may be useful in the treatment or prophylaxis of depression and other neuropsychiatric disorders.

Compounds of the present disclosure may be used to treat traumatic brain injury caused by a blast or a blast injury.

The compounds may be used to in the treatment of schizophrenia. Alternatively, the compounds may not be used to treat schizophrenia.

NMDARs play an important role in processes such as synaptic plasticity, learning, and memory. Deficits in synaptic plasticity are thought to contribute to cognitive dysfunction in a wide range of indications, including Alzheimer's disease, autism, developmental delay, cognitive disability, schizophrenia, Parkinson's disease and other neurological diseases.

The disclosure relates to methods of treating or preventing a neurological disease, condition, or disorder comprising administering an effective amount of a thienylpyrimidinone compound or derivative disclosed herein to a subject in need thereof. In certain embodiments, the condition is depression, anxiety, schizophrenia, or bipolar disorder. In certain embodiments, the compound may be administered in combination with a second psychiatric medication, e.g., anti-depressant, anti-psychotic (typical or atypical), relaxant, chlorpromazine, haloperidol, perphenazine, fluphenazine, risperidone, olanzapine, quetiapine, ziprasidone, aripiprazole, paliperidone, etc.

Optionally, the condition is a central nervous system (CNS) disorders such as those selected from Alzheimer's disease, Huntington's disease, and Amyotrophic Lateral Sclerosis (ALS). In certain embodiments, the disclosure relates to methods of improving learning or memory comprising administering an effective amount of a compound disclosed herein to a subject in need thereof.

The disclosure further relates to methods of improving synaptic plasticity, learning, and memory by administering compounds disclosed herein to subject in need thereof. Deficits in synaptic plasticity are thought to contribute to cognitive dysfunction in a wide range of indications, including Alzheimer's disease, autism, developmental delay, cognitive disability, schizophrenia, Parkinson's disease and other neurological diseases. In certain embodiments, the disclosure relates to methods of treating or preventing Alzheimer's disease, autism or autism spectrum disorders, developmental delay, cognitive disability, schizophrenia, Parkinson's disease and other neurological diseases comprising administering compounds disclosed herein to a subject in need thereof.

Certain NMDARs contain a GluN1 subunit in addition to GluN2A-GluN2D subunits. Stimulation of one or more of the subunits are thought to be beneficial for the treatment of these conditions as well as other conditions dependent on synaptic plasticity such as motor retraining and rehabilitation after ischemic insult, traumatic brain injury, spinal cord injury, and conditions that involve impairment of movement, speech, vision, or other normal functions controlled by the brain. In certain embodiments, the disclosure relates to methods of managing, improving, treating or preventing motor retraining and rehabilitation after ischemic insult, traumatic brain injury, and conditions that involve in impairment of movement, speech, vision, or other functions controlled by the brain by administering an effective amount of a compound disclosed herein to a subject in need thereof.

The disease or condition is optionally selected depression, anxiety, epilepsy, posttraumatic stress disorder, dementia, diabetic neuropathy, peripheral neuropathy, or stroke.

The methods described herein include a method of treating or reducing the risk of disorders associated with neurological disorders, and neuropsychiatric disorders in a subject. Examples of neurological and neuropsychiatric disorders include depression, anxiety, Alzheimer's, CNS injuries, and the like. This method includes the steps of selecting a subject with or at risk of developing the neurological disorder or neuropsychiatric disorder and administering to the subject a therapeutically effective amount of a compound disclosed herein. The compound can be administered systemically (e.g., orally, parenterally (e.g. intravenously), intramuscularly, intraperitoneally, transdermally (e.g., by a patch), extracorporeally, topically, by inhalation, subcutaneously or the like), by administration into the central nervous system (e.g., into the brain (intracerebrally or intra ventricularly), spinal cord, or into the cerebrospinal fluid), or any combination thereof.

The subject in need thereof can be a patient diagnosed as suffering from depression or anxiety. These diseases and their diagnoses are very clearly defined in the "Diagnostic and Statistical Manual of Mental Disorders (DSM-IV)" published by the American Psychiatric Association. This manual sets forth diagnostic criteria, descriptions and other information to guide the classification and diagnosis of mental disorders and is commonly used in the field of neuropsychiatry. For example, the subject receiving a pharmaceutical composition containing a compound disclosed herein may be co-administered an antidepressant or anti-anxiolytic medication (in combination with as a single dose or separate medication). Optionally, the patient has been diagnosed by a mental health professional (e.g., a psychiatrist) with an anxiety or depression disorder.

The disclosure contemplates the treatment of other mental disorders or conditions by administering effective amounts of compounds disclosed herein. contemplated mental disorders and conditions include, but are not limited to, acute stress disorder, adjustment disorder, adolescent antisocial behavior, adult antisocial behavior, age-related cognitive decline, agoraphobia, alcohol-related disorder, Alzheimer's, amnestic disorder, anorexia nervosa, anxiety, attention deficit disorder, attention deficit hyperactivity disorder, autophagia, bereavement, bibliomania, binge eating disorder, bipolar disorder, body dysmorphic disorder, bulimia nervosa, circadian rhythm sleep disorder, cocaine-addition, dysthymia, exhibitionism, gender identity disorder, Huntington's disease, hypochondria, multiple personality disorder, obsessive-compulsive disorder (OCD), obsessive-compulsive personality disorder (OCPD), posttraumatic stress disorder (PTSD), Rett syndrome, sadomasochism, and stuttering.

The disclosure contemplates the treatment of depression with compounds disclosed herein. Depression can be divided into several types. Major depression is the most severe form of depression characterized by a severe, persistent depressed mood and loss of interest or pleasure in normal activities accompanied by decreased energy, changes in sleep habits, restless behavior, difficulty concentrating, loss of appetite, feelings of guilt or hopelessness, and in severe cases, psychotic symptoms such as hallucinations, delusions, and even suicidal thoughts. An individual typically has a history (greater than 2 weeks) of persistent sad moods, loss of interest or pleasure in activities once enjoyed, and feelings of guilt or hopelessness, restless behavior, difficulty concentrating, and even suicidal thoughts in order to make a diagnosis of major depression. The Beck's Depression Scale Inventory, or other screen tests for depression, can be helpful in diagnosing depression.

Major depression can be treated with medications and/or counseling. Medications used include, but are not limited to, tricyclic antidepressants, monoamine oxidase inhibitors, selective serotonin re-uptake inhibitor (SSRIs), and some antidepressant drugs such as bupropion, reboxetine, trazodone, venlafaxine, and mitrazapine. Antipsychotic medications are typically administered to patients suffering from more severe forms of psychotic symptoms, such as delusions or hallucinations. Types of psychotherapy include interpersonal therapy, group therapy, and cognitive behavioral therapy.

Alternative therapeutic methods include the use of herbal products for management of chronic conditions, such as psychiatric disorders, including anxiety and depression.

A second form of depression is chronic low-grade depression, also known as dysthymia. Dysthymia is present most of the time for a period of two or more years wherein an individual experiences a decrease in his/her overall level of energy, appetite, and sleep, as well as has feelings of low self-esteem and hopelessness. These symptoms cause distress and the individual has difficulty functioning in everyday activities. These symptoms, however, are not as severe as those symptoms experienced in major depression. The cause and maintenance of these symptoms are typically due to one of the following problems: loss of a friend, substantial disappointment at work or home, prolonged or chronic illness, and alcohol or drug abuse. People who suffer from dysthymia are at an increased risk for episodes of major depression. This produces a behavioral pattern called "double depression" wherein the individual is mildly depressed most of the time, with periodic symptoms of major depression.

The least severe form of depression is a depressed mood. This is an emotional state dominated by feelings of sadness, gloominess, or emptiness, which may be associated with lack of energy. Depressed moods are usually temporary responses to an unhappy or stressful event.

The disclosure contemplates the treatment of autism spectrum disorders with compounds disclosed herein. Autism Spectrum Disorder, including Asperger Syndrome, is a spectrum of neurodevelopmental disorders characterized by dysfunction in three core behavioral dimensions: repetitive behaviors, social deficits, and cognitive deficits. The repetitive behavior domain involves compulsive behaviors, unusual attachments to objects, rigid adherence to routines or rituals, and repetitive motor mannerisms such as stereotypes and self-stimulatory behaviors. The social deficit dimension involves deficits in reciprocal social interactions, lack of eye contact, diminished ability to carry on conversation, and impaired daily interaction skills. The cognitive deficits can include language abnormalities.

Administration of compounds disclosed herein may be when a child or infant shows the early signs of signs of autism spectrum disorder or other abnormal social or behavioral development, or about the time of developmental landmarks in infants or children that show early signs of autism spectrum disorder or other abnormal or behavioral development. A therapeutic intervention administered during this period could reset the developmental trajectory of the child preventing the acquisition of second order social impairments.

The disclosure contemplates the treatment of bipolar disorders with compounds disclosed herein. Bipolar disorder affects men and women equally and typically appears between the ages of 15 and 25. As opposed to unipolar major depression, the incidence of bipolar disorder does not vary widely around the world. The exact cause is unknown, but it is linked to areas of the brain which regulate mood, and has a strong genetic component. The American Psychiatric Association's "Diagnostic and Statistical Manual of Mental Disorders" describes two types of bipolar disorder, type I and type II. The type I (formerly known as manic depressive disorder), there has been at least one full manic episode. People with this type, however, may also experience episodes of major depression. In type II disorder, periods of "hypomania" involve more attenuate (less severe) manic symptoms that alternate with at least one major depressive episode. When the patients have an acute exacerbation, they may be in a manic state, depressed state, or mixed state. The manic phase is characterized by elevated mood, hyperactivity, over-involvement in activities, inflated self-esteem, a tendency to be easily distracted, or little need for sleep. In the depressive phase, there is loss of self-esteem, withdrawal, sadness, or a risk of suicide. Either the manic or the depressive episodes can predominate and produce a few mood swings, or the patterns of the mood swing may be cyclic. While in either phase, patients may abuse alcohol or other substances, which worsens the symptoms.

Methods for treating bipolar disorders differ depending upon the state of the patient. During an acute phase, hospitalization may be required to control the symptoms. In order to reduce the risk of switching into mania, hypomania or rapid cycling, a combination of a mood stabilizer (e.g. lithium; valproate) and/or antidepressants (e.g., bupropion) is utilized for controlling bipolar disorders. Even though lithium is often utilized in controlling manic and depressive relapses, careful medical supervision along with maintaining salt intake, avoiding non-steroidal anti-inflammatory drugs, and undertaking weight-reduction diets are typically performed in order to reduce possible renal failure. Valproate also is characterized by severe side effects including nausea, vomiting, anorexia, heartburn, and diarrhea. Finally, the use of antidepressants for suppressing bipolar disorder is typically monitored in order to achieve symptomatic remission. Therefore, safer therapeutic methods are needed in the art in order to reduce the severe side effects associated with current treatments of bipolar disorders.

The disclosure contemplates the treatment of cyclothymic disorders with compounds disclosed herein. Cyclothymic disorders are similar to bipolar disorders, but less extreme. Cyclothymic disorders are characterized by stages of mild mood changes with stages of mild depression and excitement (hypomania). The changes in mood are very irregular and abrupt, but the severity of the swings is less. Cyclothymia is treated like bipolar disorders, though often not as aggressively. Thus, safer treatments are needed in the art.

The disclosure contemplates the treatment of anxiety disorders with compounds disclosed herein. Anxiety disorders, panic attacks, and agoraphobia are conditions that occur as a manifestation of primary mood disorders such as depression. Anxiety is a feeling of apprehension or fear that lingers due to an individual's perception of persistent and unrelenting stress. Anxiety is typically accompanied by various physical symptoms including twitching, trembling, muscle tension, headaches, sweating (e.g., night sweats), dry mouth, or difficulty swallowing. Some people also report dizziness, a rapid or irregular heart rate, increased rate of respiration, diarrhea, or frequent need to urinate when they are anxious. Fatigue, irritable mood, sleeping difficulties, decreased concentration, sexual problems, or nightmares are also common. Some people are more sensitive to stress and are thus more likely to develop anxiety disorders. The propensity to succumb to anxiety attacks may be due to genetic predisposition or by previous (e.g. childhood) exposure to certain stresses.

Treatment of anxiety disorders includes diagnostic tests for blood differential and thyroid function as well as an electrocardiogram (EKG). If any worrisome physical signs or symptoms do not accompany the anxiety, a referral to a mental health care professional is recommended. Psychotherapy such as cognitive-behavior therapy (CBT) along with the medication benzodiazepines is typical in severe cases of anxiety. The use of addition to these treatments, use of antidepressants such as imipramine and the selective serotonin re-uptake inhibitor (SSRI) paroxetine are also contemplated.

Further, the disclosure contemplates the treatment of panic disorders with compounds disclosed herein. Panic disorder, one of the anxiety disorders, is characterized by repeated and unexpected attacks of intense fear and anxiety. Panic attacks are usually not related to a particular situation and typically "peak" within ten minutes of their onset. The exact cause of panic disorder is unknown, but it is associated with multiple physiological factors. Panic disorder can occur with or without agoraphobia, but agoraphobia develops in one-third of cases.

The disclosure contemplates the treatment of agoraphobia with compounds disclosed herein. Agoraphobia is a disorder characterized by avoidance of crowds, and open and public places, particularly if escape or assistance is not immediately available. The development of agoraphobia may involve learned behavior, since it reflects a fear of experiencing panic attacks in unprotected settings, and sometimes the association of panic attacks with areas where they have occurred.

Symptoms of panic disorder include shortness of breath, dizziness, palpitations, trembling, sweating, choking, nausea, numbness, chest pain, hot flashes or chills, fear of dying, fear of losing control, or fear of going insane. Symptoms of agoraphobia include anxiety about being in places where escape might be difficult, fear of being alone, fear of losing control in a public place, feeling of helplessness, or feelings of detachment.

The disclosure contemplates the treatment of attention deficit disorders (ADD) with compounds disclosed herein. Symptoms include developmentally inappropriate levels of attention, concentration, activity, distractibility, and impulsivity. There are three sub-categories of attention deficit disorder: (1) attention deficit/hyperactivity disorder of the combined type; (2) attention deficit/hyperactivity disorder of the predominantly inattentive type; and (3) attention deficit/hyperactivity disorder of the predominantly hyperactive or impulsive type.

The disclosure also provides a method of treatment of sleep disorders with compounds disclosed herein. A sleep disorder is a disruptive pattern of sleep that may include difficulty: falling or staying asleep, falling asleep at inappropriate times, excessive total sleep time, or abnormal behaviors associated with sleep. There are more than 100 different disorders of sleeping and waking. They can be grouped into four main categories: problems with staying and falling asleep (insomnia, e.g.), problems with staying awake (sleep state misperception, e.g.), problems with adhering to a regular sleep schedule (hypersomnias such as narcolepsy, e.g.), and sleep disruptive behaviors (sleep walking, e.g.). Both insomnia and sleep disruptive behaviors could be direct results of a patient suffering from a psychological disorder such as depression or anxiety.

The disclosure contemplates the treatment of insomnia with the compounds disclosed herein. Insomnia includes any combination of difficulty with falling asleep, staying asleep, intermittent wakefulness, and early-morning awakening and can lead to the following disorders: psychophysiological, delayed sleep phase syndrome, hypnotic dependent disorder, and stimulant dependent sleep disorder. Episodes may be either transient (2-3 weeks) or chronic.

Sleep disruptive behaviors include sleep terror disorder, sleep walking or REM behavior disorders (a type of psychosis related to lack of REM sleep and lack of dreaming). Symptoms of sleep disruptive behaviors are depressed mood, anxiety, apathy, difficulty concentrating, irritability, daytime fatigue, drowsiness, and difficulty falling asleep.

In one aspect of the present disclosure, the psychiatric disorder to be treated is PTSD. PTSD is defined by DSM-IV as an anxiety disorder that an individual may develop following exposure to a traumatic event, and is characterized by (1) re-experiencing the traumatic event, such as recurrent nightmares, intrusive recollections of the event, flashbacks, physiological and psychological responses to internal or external cues relating to the event, etc.; (2) persistent avoidance of thoughts, people or places associated with the event; (3) numbing of general responsiveness such as emotional detachment, restricted affect or loss of interest in activities; and (4) persistence of increased arousal such as exaggerated startle response, hypervigilance, irritability, or difficulty sleeping, etc.

The disclosure contemplates the treatment of schizophrenia with compounds disclosed herein. Schizophrenia is characterized by a breakdown of thought processes and by poor emotional responsiveness and is generally accompanied by social or occupational dysfunction. It is often described in terms of positive and negative symptoms. Positive symptoms can include delusions, disorganized speech and thinking, and tactile, auditory, visual, olfactory, and gustatory hallucinations, typically regarded as manifestations of psychosis. Negative symptoms are deficits of normal emotional responses or of other thought processes such as flat or blunted affect and emotion, poverty of speech, inability to experience pleasure, lack of desire to form relationships, and lack of motivation.

The onset of schizophrenia symptoms typically occurs in young adulthood. Diagnosis typically involves the patient meeting three criteria. The first is characteristic symptoms, in which the patient experiences two or more symptoms for more than one month including delusions, hallucinations, disorganized speech, catatonic behavior, and negative symptoms. The second is social or occupational dysfunction. The third is a significant duration, generally about six months.

A subject undergoing treatment with the methods of the disclosure may exhibits an improvement in one or more symptoms associated with the psychiatric disorder. For a description of the relevant symptoms, see, for example, the DSM-IV ((1994) Diagnostic and Statistical Manual of Mental Disorders (4th ed., American Psychiatric Association, Washington D.C.)), which is herein incorporated by reference. The efficacy of the methods of the disclosure can be assessed using any clinically recognized assessment method for measuring a reduction of one or more symptoms of the particular psychiatric disorder. "Alleviation of symptoms," in the context of a behavioral disorder, refers to improvement in the social or psychological function or health of a patient, as evaluated by any measure accepted in the art. Preferably, "alleviation of symptoms" is a clinically recognizable decrease in symptoms described in DSM-IV-TR (American Psychiatric Association, 2000). The psychosocial function of a patient may be evaluated using standard measures provided in DSM-IV-TR (American Psychiatric Association, 2001), such as the Global Assessment of Functioning Scale and the Social and Occupational Functioning Assessment Scale.

Formulations

Pharmaceutical compositions disclosed herein may be in the form of pharmaceutically acceptable salts, as generally described below. Some preferred, but non-limiting examples of suitable pharmaceutically acceptable organic and/or inorganic acids are hydrochloric acid, hydrobromic acid, sulfuric acid, nitric acid, acetic acid and citric acid, as well as other pharmaceutically acceptable acids known per se (for which reference is made to the references referred to below).

When the compounds of the disclosure contain an acidic group as well as a basic group, the compounds of the disclosure may also form internal salts, and such compounds are within the scope of the disclosure. When a compound of the disclosure contains a hydrogen-donating heteroatom (e.g., NH), the disclosure also covers salts and/or isomers formed by the transfer of the hydrogen atom to a basic group or atom within the molecule.

Pharmaceutically acceptable salts of the compounds include the acid addition and base salts thereof. Suitable acid addition salts are formed from acids, which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts. Suitable base salts are formed from bases, which form non-toxic salts. Examples include the aluminum, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulphate and hemicalcium salts. For a review on suitable salts, see Handbook of Pharmaceutical Salts: Properties, Selection, and Use by Stahl and Wermuth (Wiley-VCH, 2002), incorporated herein by reference.

The compounds described herein may be administered in the form of prodrugs. A prodrug can include a covalently bonded carrier, which releases the active parent drug when administered to a mammalian subject. Prodrugs can be prepared by modifying functional groups present in the compounds in such a way that the modifications are cleaved, either in routine manipulation or in vivo, to the parent compounds. Prodrugs include, for example, compounds wherein a hydroxyl group is bonded to any group that, when administered to a mammalian subject, cleaves to form a free hydroxyl group. Examples of prodrugs include, but are not limited to, acetate, formate and benzoate derivatives of alcohol functional groups in the compounds. Methods of structuring a compound as prodrug can be found in the book of Testa and Mayer, Hydrolysis in Drug and Prodrug Metabolism, Wiley (2006). Typical prodrugs form the active metabolite by transformation of the prodrug by hydrolytic enzymes, the hydrolysis of amide, lactams, peptides, carboxylic acid esters, epoxides or the cleavage of esters of inorganic acids. It is well within the ordinary skill of the art to make an ester prodrug, e.g., acetyl ester of a free hydroxyl group. It is well known that ester prodrugs are readily degraded in the body to release the corresponding alcohol. See e.g., Imai, Drug Metab Pharmacokinet. (2006) 21(3): 173-85, entitled "Human carboxylesterase isozymes: catalytic properties and rational drug design."

Pharmaceutical compositions for use in the present disclosure typically comprise an effective amount of a compound and a suitable pharmaceutical acceptable carrier. The preparations may be prepared in a manner known per se, which usually involves mixing at least one compound according to the disclosure with one or more pharmaceutically acceptable carriers, and, if desired, in combination with other pharmaceutical active compounds, when necessary under aseptic conditions. Reference is made to U.S. Pat. No. 6,372,778, U.S. Pat. No. 6,369,086, U.S. Pat. No. 6,369,087 and U.S. Pat. No. 6,372,733 and the further references mentioned herein, as well as to the standard handbooks, such as the latest edition of Remington's Pharmaceutical Sciences.

Generally, for pharmaceutical use, the compounds may be formulated as a pharmaceutical preparation comprising at least one compound and at least one pharmaceutically acceptable carrier, diluent or excipient, and optionally one or more further pharmaceutically active compounds.

The pharmaceutical preparations of the disclosure are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use. Generally, such unit dosages will contain between 1 and 1000 mg, and usually between 5 and 500 mg, of at least one compound of the disclosure, e.g., about 10, 25, 50, 100, 200, 300 or 400 mg per unit dosage.

The compounds can be administered by a variety of routes including oral, ocular, rectal, transdermal, subcutaneous, intravenous, intramuscular or intranasal routes, depending mainly on the specific preparation used. The compound will generally be administered in an "effective amount", by which is meant any amount of a compound that, upon suitable administration, is sufficient to achieve the desired therapeutic or prophylactic effect in the subject to which it is administered. Usually, depending on the condition to be prevented or treated and the route of administration, such an effective amount will usually be between 0.01 to 1000 mg per kilogram body weight of the patient per day, more often between 0.1 and 500 mg, such as between 1 and 250 mg, for example about 5, 10, 20, 50, 100, 150, 200 or 250 mg, per kilogram body weight of the patient per day, which may be administered as a single daily dose, divided over one or more daily doses. The amount(s) to be administered, the route of administration and the further treatment regimen may be determined by the treating clinician, depending on factors such as the age, gender and general condition of the patient and the nature and severity of the disease/symptoms to be treated. Reference is made to U.S. Pat. No. 6,372,778, U.S. Pat. No. 6,369,086, U.S. Pat. No. 6,369,087 and U.S. Pat. No. 6,372,733 and the further references mentioned herein, as well as to the standard handbooks, such as the latest edition of Remington's Pharmaceutical Sciences.

For an oral administration form, the compound can be mixed with suitable additives, such as excipients, stabilizers or inert diluents, and brought by means of the customary methods into the suitable administration forms, such as tablets, coated tablets, hard capsules, aqueous, alcoholic, or oily solutions. Examples of suitable inert carriers are gum arabic, magnesia, magnesium carbonate, potassium phosphate, lactose, glucose, or starch, in particular, cornstarch. In this case, the preparation can be carried out both as dry and as moist granules. Suitable oily excipients or solvents are vegetable or animal oils, such as sunflower oil or cod liver oil. Suitable solvents for aqueous or alcoholic solutions are water, ethanol, sugar solutions, or mixtures thereof. Polyethylene glycols and polypropylene glycols are also useful as further auxiliaries for other administration forms. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, the compositions may be prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. Suitable pharmaceutical formulations for administration in the form of aerosols or sprays are, for example, solutions, suspensions or emulsions of the compounds of the disclosure or their physiologically tolerable salts in a pharmaceutically acceptable solvent, such as ethanol or water, or a mixture of such solvents. If required, the formulation may additionally contain other pharmaceutical auxiliaries such as surfactants, emulsifiers and stabilizers as well as a propellant.

For subcutaneous or intravenous administration, the compounds, if desired with the substances customary therefore such as solubilizers, emulsifiers or further auxiliaries are brought into solution, suspension, or emulsion. The compounds may also be lyophilized and the lyophilizates obtained used, for example, for the production of injection or infusion preparations. Suitable solvents are, for example, water, physiological saline solution or alcohols, e.g. ethanol, propanol, glycerol, sugar solutions such as glucose or mannitol solutions, or mixtures of the various solvents mentioned. The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, the formulations may be prepared by mixing the compounds of Formula I with a suitable non-irritating excipient, such as cocoa butter, synthetic glyceride esters or polyethylene glycols, which are solid at ordinary temperatures, but liquefy and/or dissolve in the rectal cavity to release the drug.

It is contemplated that these compositions can be extended release formulations. Typical extended release formations utilize an enteric coating. Typically, a barrier is applied to oral medication that controls the location in the digestive system where it is absorbed. Enteric coatings prevent release of medication before it reaches the small intestine. Enteric coatings may contain polymers of polysaccharides, such as maltodextrin, xanthan, scleroglucan dextran, starch, alginates, pullulan, hyaluronic acid, chitin, chitosan and the like; other natural polymers, such as proteins (albumin, gelatin etc.), poly-L-lysine; sodium poly (acrylic acid); poly(hydroxyalkylmethacrylates) (for example poly(hydroxyethyl methacrylate)); carboxypolymethylene (for example Carbopol™); carbomer; polyvinyl pyrrolidone; gums, such as guar gum, gum arabic, gum karaya, gum ghatti, locust bean gum, tamarind gum, gellan gum, gum tragacanth, agar, pectin, gluten and the like; poly(vinyl alcohol); ethylene vinyl alcohol; polyethylene glycol (PEG); and cellulose ethers, such as hydroxymethyl cellulose (HMC), hydroxyethylcellulose (HEC), hydroxypropylcellulose (HPC), methylcellulose (MC), ethylcellulose (EC), carboxyethylcellulose (CEC), ethylhydroxy ethylcellulose (EHEC), carboxymethylhydroxyethylcellulose (CMHEC), hydroxypropylmethyl-cellulose (HPMC), hydroxypropylethylcellulose (HPEC) and sodium carboxymethylcellulose (Na CMC); as well as copolymers and/or (simple) mixtures of any of the herein polymers.

Certain of the herein-mentioned polymers may further be crosslinked by way of standard techniques. The choice of polymer will be determined by the nature of the active ingredient/drug that is employed in the composition of the disclosure as well as the desired rate of release. In particular, it will be appreciated by the skilled person, for example in the case of HPMC, that a higher molecular weight will, in general, provide a slower rate of release of drug from the composition. Furthermore, in the case of HPMC, different degrees of substitution of methoxyl groups and hydroxypropoxyl groups will give rise to changes in the rate of release of drug from the composition. In this respect, and as stated above, it may be desirable to provide compositions of the disclosure in the form of coatings in which the polymer carrier is provided by way of a blend of two or more polymers of, for example, different molecular weights in order to produce a particular required or desired release profile.

Microspheres of polylactide, polyglycolide, and their copolymers poly(lactide-co-glycolide) may be used to form sustained-release protein delivery systems. Proteins can be entrapped in the poly(lactide-co-glycolide) microsphere depot by a number of methods, including formation of a water-in-oil emulsion with water-borne protein and organic solvent-borne polymer (emulsion method), formation of a solid-in-oil suspension with solid protein dispersed in a solvent-based polymer solution (suspension method), or by dissolving the protein in a solvent-based polymer solution (dissolution method). One can attach poly(ethylene glycol) to proteins (PEGylation) to increase the in vivo half-life of circulating therapeutic proteins and decrease the chance of an immune response.

The examples below are intended to further illustrate certain aspects of the methods and compositions described herein, and are not intended to limit the scope of the claims.

EXAMPLES

Example 1: Synthesis of Thieno[2,3-d]pyrimidin-4-one derivatives

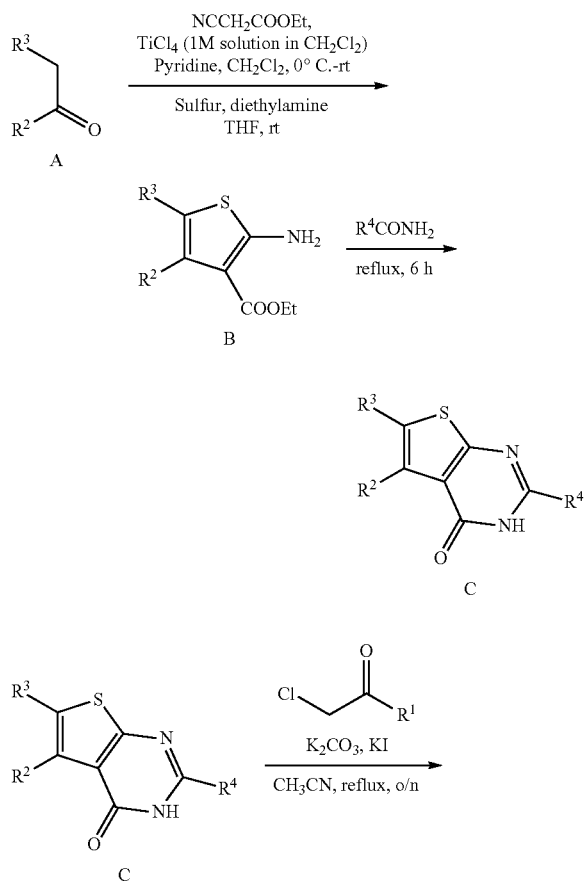

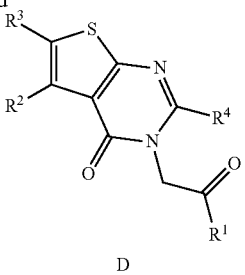

D

General Experimental Procedure for the Synthesis of Thienopyrimidinone Derivatives:

Step 1: Ketone (A) (10 mmol) and ethyl cyanoacetate (12 mmol) were dissolved in dichloromethane (DCM; 40 mL) and a $TiCl_4$ 1M solution in DCM (20 mmol) was added dropwise at 0° C. The reaction mixture was stirred for 30 minutes at 0° C. and then dry pyridine (0.8 equiv, 8 mmol) was added dropwise. The ice bath was removed and the reaction mixture was stirred for 1 hour. A further aliquot of pyridine (2.4 equiv, 24 mmol) was added dropwise and the reaction mixture was stirred overnight at room temperature. The mixture was poured into a 3M HCl solution (40 mL) and the organic layer was separated. The aqueous layer was extracted with DCM (2×20 mL) and the combined organic layers were washed with water and brine. The organic layer was dried over anhydrous $MgSO_4$, filtered, and concentrated to give the crude product. The crude product was dissolved in tetrahydrofuran (THF; 8 mL) and then sulfur was added (1.25 equiv, 12.5 mmol) followed by diethylamine (4.0 equiv., 40 mmol) dropwise at room temperature. The solution was stirred for 2 hours at room temperature. The mixture was diluted with diethyl ether and washed with water and brine. The organic layer was dried over $MgSO_4$, filtered, and concentrated to give the crude thiophene amino compound. The crude product was purified by flash column chromatography using silica gel as the solid phase and ethyl acetate in hexanes as the eluent to give the pure thiophene amino compound (B).

Step 2: The thiophene amine (B) (5 mmol) was suspended in formamide (10 mL, 0.5M) and stirred for 6 hours at 170° C. The reaction mixture was cooled to 10° C., stirred for 3 hours, and filtered. The solid was washed thoroughly with chilled ethanol and dried under vacuum to give the pure thienopyramidinone (C).

Step 3: To a suspension of thienopyramidinone (C) in acetonitrile were sequentially added $K_2CO_3$, KI, and alkyl halide. The reaction mixture was refluxed overnight under argon. The reaction mixture was then concentrated under vacuum and purified by silica gel column chromatography using 1-2% of methanol in dichloromethane as the eluent to give the pure Thieno[2,3-d]pyrimidin-4-one (D).

Scheme 5. Modification to aryl substituent

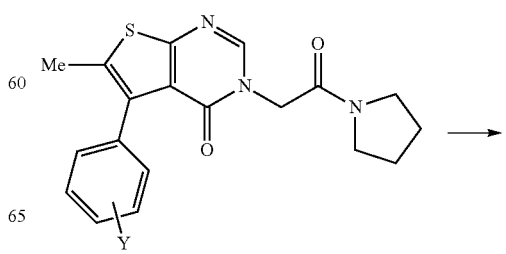

37

-continued

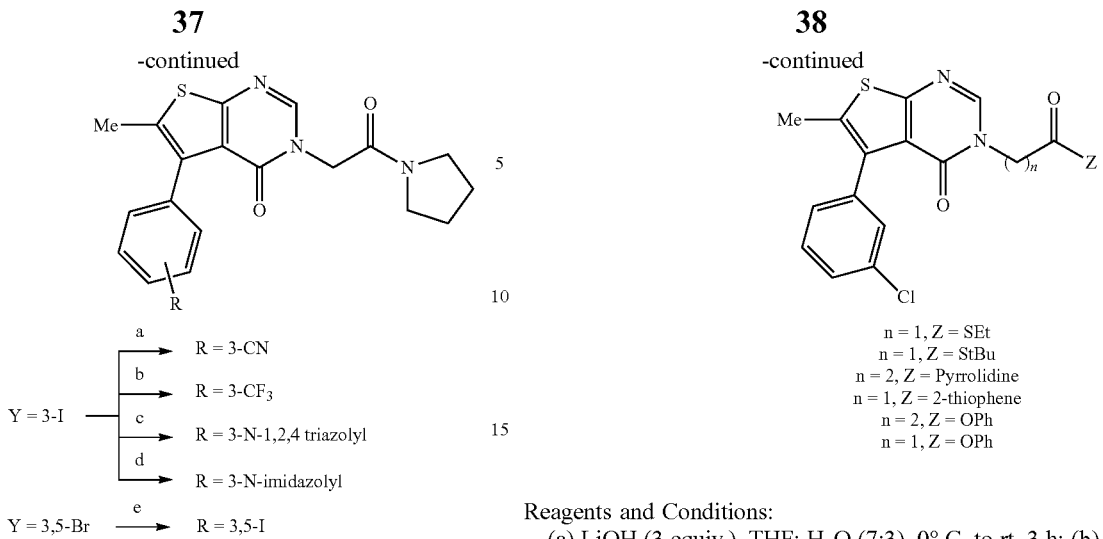

Reagents and Conditions:

(a) CuI (10 mol %), 1, 10 phenanthroline (20 mol %), K₄[Fe(CN)₆] (2 equiv.), Na₂CO₃, DMF, 140° C., 48 h, 79%; (b) CuI (10 mol %), CF₃COONa, DMF, 150° C., 48 h, 71%; (c) CuI (5 mol %), trans-N,N'-Dimethylcyclohexane-1,2-diamine (10 mol %), K₃PO₄ (2.2 equiv.), 1, 2, 4-triazole, DMF, 110° C., 24 h, 78%; (d) CuI (5 mol %), trans-N,N'-Dimethylcyclohexane-1,2-diamine (10 mol %), K₃PO₄ (2.2 equiv.), imidazole, DMF, 110° C., 24 h, 61%; (e) CuI (10 mol %), N,N'-Dimethylethyl-1,2-diamine (20 mol %), NaI (2.0 equiv.), p-dioxane, 110° C., 71%.

Scheme 6. Modification of part B n = 1
n = 2

38

-continued n = 1, Z = SEt
n = 1, Z = StBu
n = 2, Z = Pyrrolidine
n = 1, Z = 2-thiophene
n = 2, Z = OPh
n = 1, Z = OPh Reagents and Conditions:

(a) LiOH (3 equiv.), THF: H₂O (7:3), 0° C. to rt, 3 h; (b) EDCI.HCl, DMAP, EtSH, CH₂Cl₂, rt, 48 h, 31%; (c) EDCI.HCl, DMAP, tBuSH, CH₂Cl₂, rt, 48 h, 35%; (d) EDCI.HCl, DMAP, pyrrolidine, CH₂Cl₂, rt, 48 h, 30%; (e) BiT (1 equiv.), TPP (1 equiv.), DMF, 3 h, 50° C., CuMeS (20 mol %), N-methylimidazole (40 mol %), 2-ThB(OH)₂, 50° C., 24 h, 26%.

Exemplary Compounds

Compounds according to Formula I were synthesized using the general methods shown above. Exemplary synthesized compounds and the characterization data for the synthesized compounds are provided below:

1622-28

1622-28:
¹H NMR (CDCl₃, 400 MHz): δ 1.26 (3H, t, J=7.1 Hz), 2.37 (3H, s), 4.21 (2H, q, J=7.1 Hz), 4.64 (2H, s), 7.17-7.22 (1H, m), 7.28 (1H, s), 7.31-7.38 (2H, m), 7.91 (1H, s). ¹³C NMR (CDCl₃, 100 MHz): δ 13.9, 13.9, 46.7, 62.0, 122.1, 127.6, 128.4, 128.8, 130.0, 132.9, 133.4, 134.8, 136.2, 145.9, 156.4, 161.7, 167.1.

1622-29

1622-29:
¹H NMR (dmso-d₆, 400 MHz): δ 2.33 (3H, s), 4.65 (2H, s), 7.21-7.29 (1H, m), 7.33 (1H, s), 7.39-7.49 (4H, m), 8.39

(1H, s). ¹³C NMR (dmso-d₆, 100 MHz): δ 13.6, 47.0, 121.2, 127.2, 128.9, 129.3, 129.9, 132.1, 132.1, 133.9, 136.3, 148.1, 155.9, 161.3, 169.2.

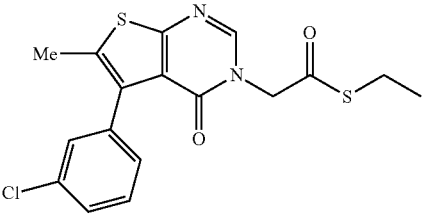

1622-30

1622-30:

¹H NMR (CDCl₃, 400 MHz): δ 1.24 (3H, t, J=7.4 Hz), 2.36 (3H, s), 2.92 (2H, q, J=7.4 Hz), 4.79 (2H, s), 7.16-7.21 (1H, m), 7.28 (1H, s), 7.31-7.36 (2H, m), 7.89 (1H, s). ¹³C NMR (CDCl₃, 100 MHz): δ 13.9, 14.2, 23.5, 53.6, 122.1, 127.6, 128.4, 128.9, 130.0, 133.0, 133.4, 134.9, 136.1, 145.9, 156.2, 161.7, 193.5.

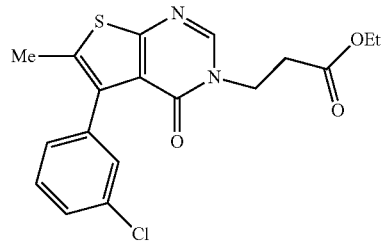

1622-31

1622-31:

¹H NMR (CDCl₃, 400 MHz): δ 1.21 (3H, t, J=7.1 Hz), 2.36 (3H, s), 2.79 (2H, t, J=6.0 Hz), 4.11 (2H, q, J=7.1 Hz), 4.18 (2H, t, J=6.0 Hz), 7.17-7.22 (1H, m), 7.29 (1H, s), 7.33-7.37 (2H, m), 8.15 (1H, s). ¹³C NMR (CDCl₃, 100 MHz): δ 13.9, 14.0, 32.8, 43.0, 60.9, 122.2, 127.6, 128.4, 128.8, 130.0, 132.8, 133.4, 134.4, 136.3, 146.9, 156.7, 161.8, 171.2.

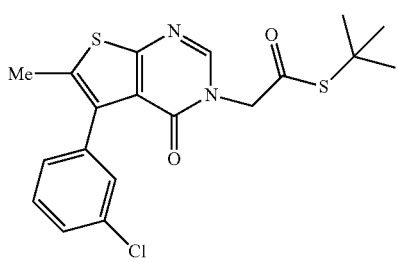

1622-32

1622-32:

¹H NMR (CDCl₃, 400 MHz): δ 1.45 (9H, s), 2.36 (3H, s), 4.74 (2H, s), 7.18-7.23 (1H, m), 7.28 (1H, s), 7.31-7.38 (2H, m), 7.88 (1H, s). ¹³C NMR (CDCl₃, 100 MHz): δ 13.9, 29.6, 29.8, 49.6, 53.5, 122.1, 127.6, 128.4, 128.9, 130.1, 133.1, 133.4, 134.8, 136.2, 140.0, 156.1, 161.7, 193.5.

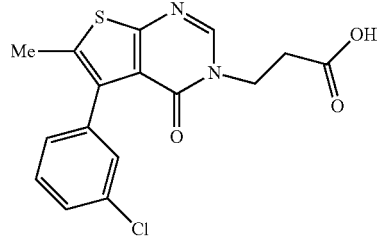

1622-33

1622-33:

¹H NMR (dmso-d₆, 400 MHz): δ 2.31 (3H, s), 2.66 (2H, t, J=6.6 Hz), 4.0 (2H, t, J=6.6 Hz), 7.30-7.22 (1H, m), 7.36 (1H, m), 7.47-7.38 (2H, m), 8.39 (1H, s). ¹³C NMR (dmso-d₆, 100 MHz): δ 13.6, 32.5, 42.4, 121.3, 127.1, 129.0, 129.2, 130.0, 132.1, 132.1, 133.4, 136.4, 148.3, 156.0, 161.2, 172.3.

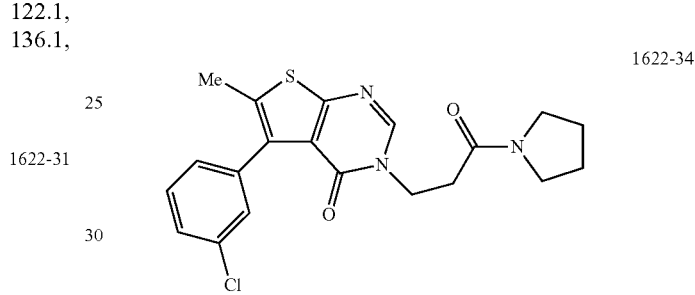

1622-34

1622-34:

¹H NMR (CDCl₃, 400 MHz): δ 1.93-1.71 (4H, m), 2.34 (3H, s), 2.71 (2H, t, J=5.6 Hz), 3.27 (2H, t, J=6.6 Hz), 3.40 (2H, t, J=6.6 Hz), 4.25 (2H, t, J=5.6 Hz), 7.22-7.17 (1H, m), 7.28 (1H, m), 7.38-7.32 (2H, m), 8.35 (1H, s). ¹³C NMR (CDCl₃, 100 MHz): δ 13.9, 24.2, 25.9, 33.0, 43.0, 45.6, 46.3, 122.1, 127.5, 128.5, 128.8, 130.1, 132.6, 133.4, 134.1, 136.5, 147.8, 157.1, 162.0, 168.4.

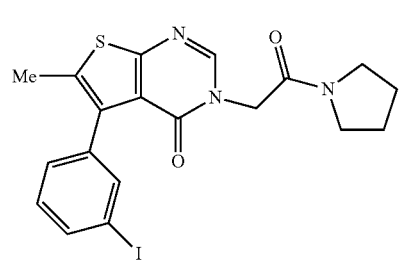

1622-35

1622-35:

¹H NMR (CDCl₃, 400 MHz): δ). 1.85 (2H, quint, J=6.9 Hz), 1.99 (2H, quint, J=6.8 Hz), 3.47 (2H, t, J=6.9 Hz), 3.52 (2H, t, J=6.8 Hz), 4.65 (2H, s), 7.24 (1H, dt, J=7.7, 1.5 Hz), 7.28 (1H, t, J=7.7 Hz), 7.44 (1H, t, J=1.5 Hz), 7.48 (1H, dt, J=7.6, 1.5 Hz), 7.98 (1H, s 2.35 (3H, s). ¹³C NMR (CDCl₃, 100 MHz): δ 13.9, 24.0, 25.9, 45.8, 46.2, 46.3, 121.6, 122.0, 128.9, 129.1, 130.4, 132.8, 132.8, 134.4, 136.7, 146.8, 156.6, 161.9, 164.0.

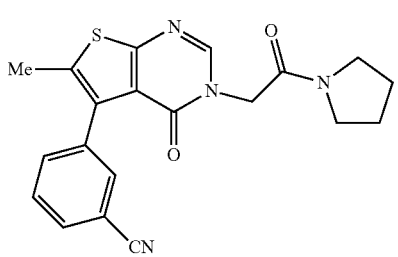

1622-36

1622-36:

¹H NMR (CDCl₃, 400 MHz): δ 7.98 (1H, s), 7.64 (1H, dt, J=7.4, 1.5 Hz), 7.60 (1H, t, J=1.4 Hz), 7.55 (1H, dt, J=7.8, 1.5 Hz), 7.50 (1H, t, J=7.5 Hz), 4.64 (2H, s), 3.52 (2H, t, J=6.8 Hz), 3.46 (2H, t, J=6.9 Hz), 2.35 (3H, s), 1.99 (2H, quint, J=6.8 Hz), 1.85 (2H, quint, J=6.9 Hz). ¹³C NMR (CDCl₃, 100 MHz): δ 13.9, 24.0, 26.0, 45.8, 46.2, 46.4, 111.8, 118.8, 121.8, 128.4, 131.0, 131.9, 133.7, 134.7, 134.9, 135.9, 146.9, 156.6, 162.1, 163.9.

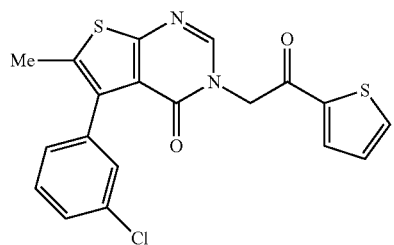

1622-37

1622-37:

¹H NMR (CDCl₃, 400 MHz): δ 7.92 (1H, s), 7.82 (1H, d, J=3.8 Hz), 7.71 (1H, d, J=4.9 Hz), 7.37-7.27 (3H, m), 7.22-7.14 (2H, m), 5.26 (2H, s), 2.36 (3H, s). ¹³C NMR (CDCl₃, 100 MHz): δ 13.9, 50.6, 122.1, 127.6, 128.4, 128.4, 128.8, 130.0, 132.8, 132.9, 133.4, 134.7, 135.1, 136.3, 140.4, 146.3, 156.4, 161.9, 184.3.

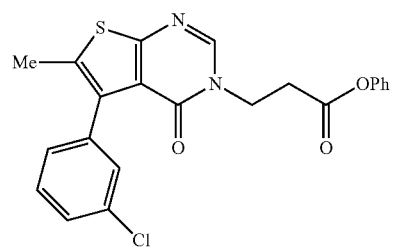

1622-38

1622-38:

¹H NMR (CDCl₃, 400 MHz): δ 8.09 (1H, s), 7.36-7.21 (5H, m), 7.19-7.10 (2H, m), 6.97-6.91 (2H, m), 4.19 (2H, t, J=6.0 Hz), 3.00 (2H, t, J=6.0 Hz), 2.29 (3H, s). ¹³C NMR (CDCl₃, 100 MHz): δ 13.9, 32.9, 42.9, 121.3, 122.2, 126.1, 127.6, 128.5, 128.9, 129.4, 130.1, 132.8, 133.4, 134.6, 136.3, 146.7, 150.1, 156.8, 161.9, 170.0.

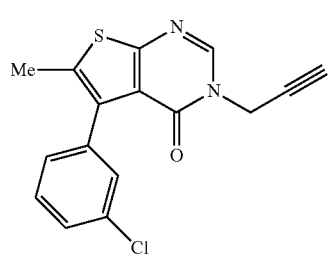

1622-39

1622-39:

¹H NMR (CDCl₃, 400 MHz): δ 8.27 (1H, s), 7.41-7.32 (2H, m), 7.29 (1H, brs), 7.24-7.14 (1H, m), 4.72 (2H, d, J=2.5 Hz), 2.48 (1H, t, J=2.5 Hz), 2.36 (3H, s). ¹³C NMR (CDCl₃, 100 MHz): δ 13.9, 34.7, 75.5, 76.3, 121.9, 127.6, 128.4, 128.9, 130.0, 132.9, 133.5, 134.9, 136.2, 144.7, 156.0, 161.6.

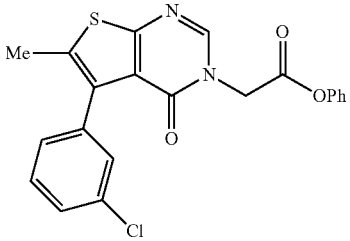

1622-40

1622-40:

¹H NMR (CDCl₃, 400 MHz): δ 8.00 (1H, s), 7.40-7.33 (4H, m), 7.31 (1H, m), 7.27-7.18 (2H, m), 7.10 (2H, d, J=8.7 Hz), 4.87 (2H, s), 2.38 (3H, s). ¹³C NMR (CDCl₃, 100 MHz): δ 13.9, 47.0, 121.1, 122.1, 126.3, 127.7, 128.4, 128.9, 129.5, 130.1, 133.0, 133.5, 135.1, 136.1, 145.7, 150.0, 156.4, 161.8, 165.8.

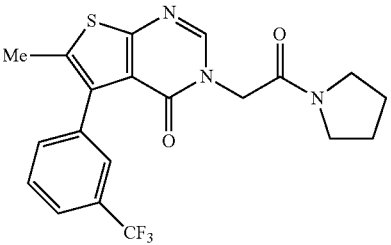

1622-42

1622-42:

¹H NMR (CDCl₃, 400 MHz): δ 1.83 (2H, quint, J=6.8 Hz), 1.96 (2H, J=6.9 Hz), 2.34 (3H, s), 3.44 (2H, t, J=6.9 Hz), 3.49 (2H, t, J=6.8 Hz), 4.64 (2H, s), 7.48-7.53 (2H, m), 7.54 (1H, s), 7.56-7.62 (1H, m), 7.98 (1H, s). ¹³C NMR (CDCl₃, 100 MHz): δ 13.8, 23.9, 25.9, 45.7, 46.2, 46.4, 121.9, 124.1 (q, J=272.3 Hz), 124.1 (q, J=3.8 Hz), 126.8 (q, J=3.8 Hz), 127.9, 129.8 (q, J=32.1 Hz), 132.8, 133.7, 134.5, 135.3, 146.9, 156.6, 161.9, 164.0.

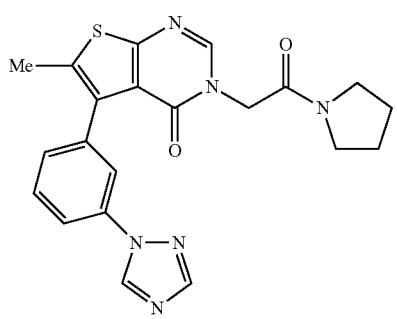

1622-43

1622-43:

¹H NMR (CDCl₃, 400 MHz): δ 1.84 (2H, quint, J=6.8 Hz), 1.97 (2H, quint, J=6.8 Hz), 2.39 (3H, s), 3.45 (2H, t, J=6.8 Hz), 3.50 (2H, t, J=6.8 Hz), 4.64 (s, 2H), 7.34 (1H, dt, J=7.6, 1.4, 1.0 Hz), 7.54 (1H, t, J=7.8 Hz), 7.63 (1H, t, J=1.4 Hz), 7.68 (1H, ddd, J=8.0, 2.1, 1.0 Hz), 7.98 (1H, s), 8.08 (1H, s), 8.57 (1H, s). ¹³C NMR (CDCl₃, 100 MHz): δ 14.0, 24.0, 25.9, 45.8, 46.2, 46.5, 119.0, 121.8, 122.0, 129.0, 129.9, 132.7, 134.6, 136.3, 136.5, 141.0, 146.8, 152.4, 156.7, 162.1, 163.9.

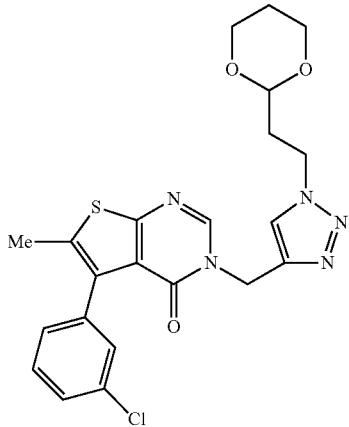

1622-44

1622-44:

¹H NMR (CDCl₃, 400 MHz): δ 1.21-1.34 (1H, m), 1.93-2.08 (1H, m), 2.12 (2H, td, J=6.9, 4.8 Hz), 2.34 (3H, s), 3.65 (2H, td, J=12.0, 2.5 Hz), 4.03 (2H, dd, J=10.6, 4.9 Hz), 4.41 (2H, t, J=7.0 Hz), 4.47 (1H, t, J=4.8 Hz), 5.17 (2H, s), 7.15-7.22 (1H, m), 7.26-7.28 (1H, m), 7.33-7.37 (2H, m), 7.65 (1H, s), 8.30 (1H, s). ¹³C NMR (CDCl₃, 100 MHz): δ 13.9, 25.5, 35.1, 41.1, 45.3, 66.7, 98.8, 122.2, 124.3, 127.6, 128.4, 128.8, 130.1, 132.8, 133.4, 134.7, 136.4, 141.8, 146.0, 156.5, 161.9.

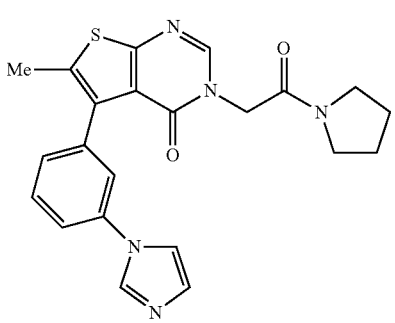

1622-45

1622-45:

¹H NMR (CDCl₃, 400 MHz): δ 2.37 (3H, s), 5.27 (2H, s), 7.10-7.18 (1H, m), 7.20-7.30 (2H, m), 7.41-7.50 (2H, m), 7.69-7.74 (1H, m), 7.80-7.85 (1H, m), 7.92 (1H, s). ¹³C NMR (CDCl₃, 100 MHz): δ 13.9, 50.6, 121.6, 122.1, 128.4, 128.9, 129.1, 130.4, 132.8, 134.7, 135.1, 136.5, 138.6, 140.4, 146.3, 156.4, 161.8, 184.3.

1622-46

1622-46:

¹H NMR (CDCl₃, 400 MHz): δ 1.82 (2H, quint, J=6.9 Hz), 1.95 (2H, quint, J=6.8 Hz), 2.36 (3H, s), 3.43 (2H, t, J=6.9 Hz), 3.48 (2H, t, J=6.8 Hz), 4.63 (2H, s), 7.17 (1H, brs), 7.28-7.40 (4H, m), 7.48 (2H, t, J=7.7 Hz), 7.88 (1H, brs), 7.97 (1H, s). ¹³C NMR (CDCl₃, 100 MHz): δ 13.9, 23.9, 25.8, 45.7, 46.1, 46.4, 118.5, 120.1, 121.8, 123.3, 128.9, 129.1, 130.2, 132.7, 134.3, 136.4, 136.5, 146.8, 146.8, 156.6, 162.0, 163.9.

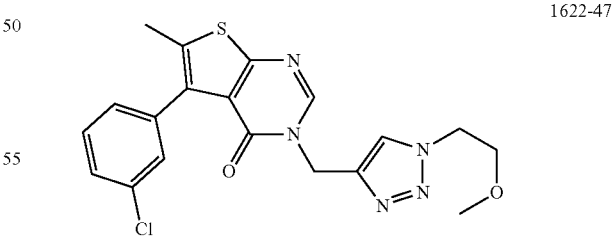

1622-47

1622-47:

¹H NMR (CDCl₃, 400 MHz): δ 2.34 (3H, s), 3.31 (3H, s), 3.70 (2H, t, J=5.0 Hz), 4.46 (2H, t, J=5.0 Hz), 5.19 (2H, s), 7.16-7.24 (1H, m), 7.26-7.28 (1H, m), 7.34-7.38 (2H, m), 7.76 (1H, s). ¹³C NMR (CDCl₃, 100 MHz): δ 13.9, 40.9, 50.2, 58.9, 70.4, 122.2, 124.7, 127.6, 128.4, 128.8, 130.1, 132.8, 133.4, 134.6, 136.4, 141.9, 146.0, 156.5, 161.8.

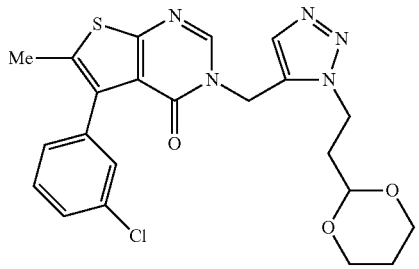

1622-48

1622-48:

¹H NMR (CDCl₃, 400 MHz): δ 1.17-1.33 (1H, m), 1.85-2.01 (3H, m), 2.32 (3H, s), 3.63 (2H, tt, J=12.0, 2.6 Hz), 3.98 (4H, t, J=6.5 Hz), 4.52 (1H, t, J=4.6 Hz), 4.76 (2H, ABq, J=53.5, 15.1 Hz), 7.07-7.14 (1H, m), 7.20-7.23 (1H, m), 7.25-7.28 (1H, m), 7.28-7.33 (2H, m), 8.25 (1H, s). ¹³C NMR (CDCl₃, 100 MHz): δ 13.9, 25.4, 34.2, 40.4, 44.2, 66.6, 98.7, 121.4, 122.0, 127.4, 128.5, 128.7, 130.1, 132.7, 133.2, 134.6, 136.5, 143.8, 146.3, 156.1, 161.8.

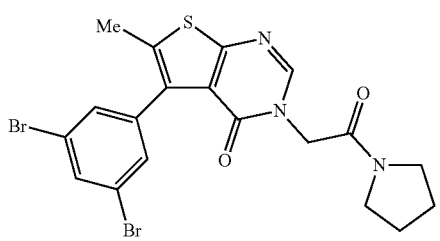

1622-49

1622-49:

¹H NMR (CDCl₃, 400 MHz): δ 1.86 (2H, quint, J=6.9 Hz), 2.00 (2H, quint, J=6.8 Hz), 2.35 (3H, s), 3.47 (2H, t, J=6.9 Hz), 3.54 (2H, t, J=6.8 Hz), 4.65 (2H, s), 7.38 (2H, d, J=1.7 Hz), 7.64 (1H, t, J=1.7 Hz), 7.98 (1H, s). ¹³C NMR (CDCl₃, 100 MHz): δ 13.9, 24.0, 26.0, 45.9, 46.3, 46.4, 121.9, 122.0, 131.3, 131.8, 133.0 135.1, 138.2 146.9, 156.5, 162.0, 164.0.

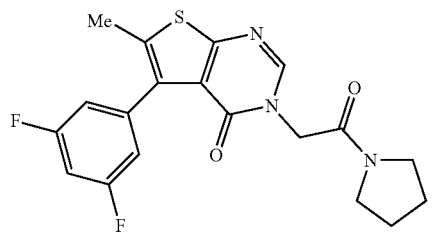

1622-50

1622-50:

¹H NMR (CDCl₃, 400 MHz): δ 1.85 (2H, quint, J=6.9 Hz), 1.99 (2H, quint, J=6.8 Hz), 2.34 (3H, s), 3.47 (2H, t, J=6.9 Hz), 3.52 (2H, t, J=6.8 Hz), 4.65 (2H, s), 6.74-6.88 (3H, m), 7.98 (1H, s). ¹³C NMR (CDCl₃, 100 MHz): δ 13.8, 24.0, 26.0, 45.8, 46.2, 46.4, 103.0 (t, J=25 Hz), 113.2 (d, J=25 Hz), 121.9, 132.0, 134.7, 137.9, 146.9, 156.5, 162.0, 162.1 (d, J=247 Hz), 162.2 (d, J=247 Hz), 163.9.

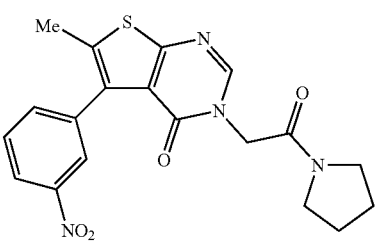

1622-51

1622-51:

¹H NMR (CDCl₃, 400 MHz): δ 1.85 (2H, quint, J=6.9 Hz), 1.98 (2H, quint, J=6.8 Hz), 2.38 (3H, s), 3.46 (2H, t, J=6.9 Hz), 3.51 (2H, t, J=6.8 Hz), 4.65 (2H, s), 7.57 (1H, t, J=7.7 Hz), 7.65 (1H, d, J=7.5 Hz), 8.00 (1H, s), 8.18 (1H, s), 8.21 (1H, d, J=8.1 Hz). ¹³C NMR (CDCl₃, 100 MHz): δ 13.9, 24.0, 25.9, 45.8, 46.2, 46.4, 121.8, 122.4, 125.1, 128.4, 131.7, 135.1, 136.2, 136.5, 146.9, 147.6, 156.7, 162.2, 163.9.

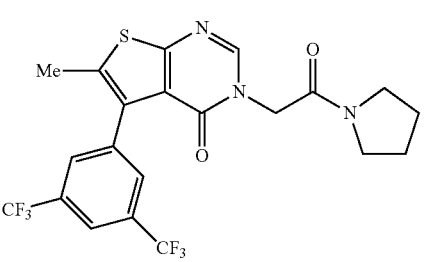

1622-53

1622-53:

¹H NMR (CDCl₃, 400 MHz): δ 1.86 (2H, quint, J=6.9 Hz), 1.99 (2H, quint, J=6.8 Hz), 2.38 (3H, s), 3.47 (2H, t, J=6.9 Hz), 3.54 (2H, t, J=6.8 Hz), 4.65 (2H, s), 7.77 (2H, s), 7.85 (1H, s), 8.01 (1H, s). ¹³C NMR (CDCl₃, 100 MHz): δ 13.8, 24.0, 25.9, 45.8, 46.2, 46.4, 121.2 (broad), 121.6, 123.3 (q, J=272 Hz), 130.6 (broad), 130.7 (q, J=33 Hz), 131.2, 135.4, 136.5, 147.1, 156.6, 162.2, 163.9.

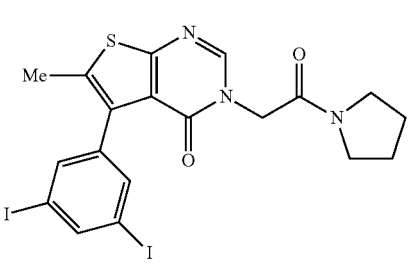

1622-54

1622-54:

¹H NMR (CDCl₃, 400 MHz): δ 1.87 (2H, quint, J=6.9 Hz), 2.01 (2H, quint, J=6.8 Hz), 2.34 (3H, s), 3.48 (2H, t, J=6.9 Hz), 3.55 (2H, t, J=6.8 Hz), 4.65 (2H, s), 7.60 (2H, s), 7.98 (1H, s), 8.02 (1H, s). ¹³C NMR (CDCl₃, 100 MHz): δ 13.9, 24.0, 26.0, 45.9, 46.3, 46.4, 93.8, 121.8, 131.1, 134.9, 138.2, 138.3, 143.8, 146.9, 156.5, 161.9, 164.0.

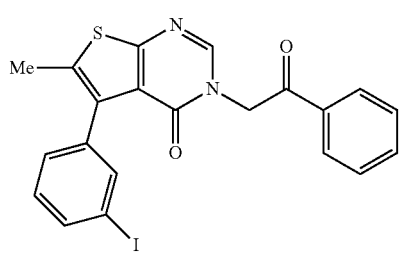

1622-57

1622-57:

¹H NMR (CDCl₃, 400 MHz): δ 2.37 (3H, s), 5.34 (2H, s), 7.20-7.28 (2H, m), 7.40-7.51 (3H, m), 7.60 (1H, t, J=7.3 Hz), 7.88 (1H, s), 7.94 (2H, d, J=7.3 Hz). ¹³C NMR (CDCl₃, 100 MHz): δ 13.9, 50.7, 121.5, 122.1, 128.0, 128.8, 129.1, 130.4, 132.8, 132.9, 134.1, 134.1, 134.2, 134.6, 136.6, 146.3, 156.5, 161.9, 191.4.

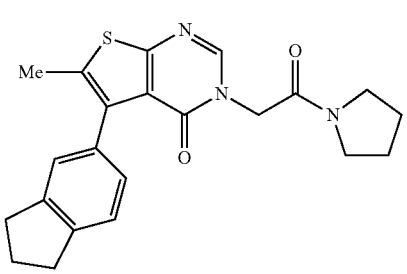

1622-59

1622-59:

¹H NMR (CDCl₃, 400 MHz): δ 1.83 (2H, quint, J=6.7 Hz), 1.96 (2H, quint, J=6.9 Hz), 2.08 (2H, quint, J=7.4 Hz), 2.34 (3H, s), 2.93 (4H, td, J=7.2, 2.7 Hz), 3.44 (2H, t, J=6.9 Hz), 3.48 (2H, t, J=6.7 Hz), 4.64 (2H, s), 7.05 (1H, d, J=7.6 Hz), 7.13 (1H, s), 7.24 (1H, d, J=7.6 Hz), 7.96 (1H, s). ¹³C NMR (CDCl₃, 100 MHz): δ 13.9, 23.9, 25.2, 25.9, 32.6, 32.7, 45.6, 46.1, 46.2, 122.3, 123.4, 125.8, 127.9, 132.4, 133.2, 134.9, 143.1, 143.3, 146.6, 156.7, 161.6, 164.1.

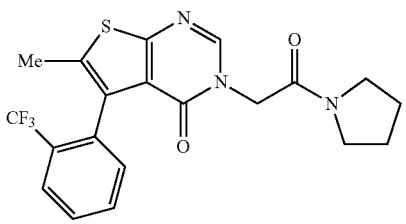

1622-60

1622-60:

¹H NMR (CDCl₃, 400 MHz): δ 1.81 (2H, m), 1.92 (2H, quint, J=6.8 Hz), 2.18 (3H, s), 3.35-3.49 (4H, m), 4.60 (2H, ABq, J=161.0, 16.0 Hz), 7.27 (1H, d, J=7.5 Hz), 7.48 (1H, t, J=7.6 Hz), 7.56 (1H, t, J=7.3 Hz), 7.73 (1H, d, J=7.7 Hz), 7.94 (1H,$). ¹³C NMR (CDCl₃, 100 MHz): δ 13.7, 23.9, 25.9, 45.6, 45.9, 46.1, 123.3, 123.8 (q, J=273 Hz), 125.7, 127.8, 129.3 (q, J=29 Hz), 130.5, 131.3, 131.6, 134.4, 134.8, 146.8, 156.4, 161.2, 164.0.

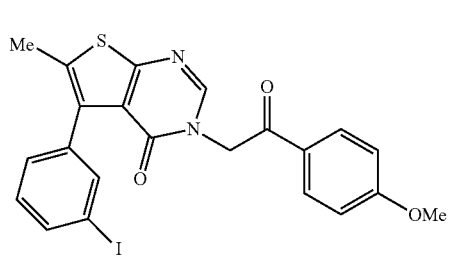

1622-61

1622-61:

¹H NMR (CDCl₃, 400 MHz): δ 2.37 (3H, s), 3.86 (3H, s), 5.31 (2H, s), 6.93 (2H, d, J=8.7 Hz), 7.25 (2H, d, J=6.9 Hz), 7.44 (1H, s), 7.89 (1H, s), 7.93 (1H, d, J=8.7 Hz). ¹³C NMR (CDCl₃, 100 MHz): δ 13.9, 50.3, 55.5, 114.0, 121.6, 122.1, 127.1, 128.9, 129.1, 130.4, 130.4, 132.8, 132.8, 134.5, 136.6, 146.5, 156.5, 161.9, 164.3, 189.8.

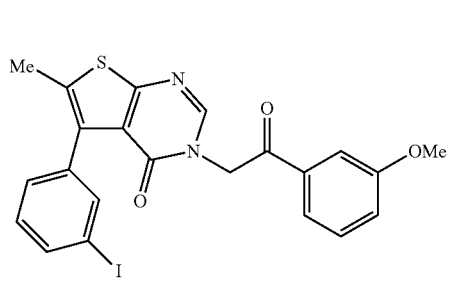

1622-62

1622-62:

¹H NMR (CDCl₃, 400 MHz): δ 2.37 (3H, s), 3.83 (3H, s), 5.35 (2H, s), 7.15 (1H, d, J=8.2 Hz), 7.25 (2H, d, J=5.2 Hz), 7.38 (1H, t, J=8.1 Hz), 7.45 (2H, m), 7.54 (1H, d, J=7.6 Hz), 7.89 (1H, s). ¹³C NMR (CDCl₃, 100 MHz): δ 13.9, 50.8, 55.4, 122.2, 120.5, 120.8, 121.6, 122.1, 128.9, 129.1, 129.8, 130.5, 132.8, 132.9, 134.7, 135.4, 136.6, 146.4, 156.5, 159.9, 161.9, 191.3.

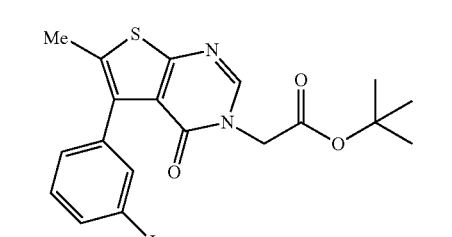

1622-63

1622-63:

¹H NMR (CDCl₃, 400 MHz): δ 1.45 (9H, s), 2.36 (3H, s), 4.56 (2H, s), 7.24 (1H, dt, J=7.6, 1.4 Hz), 7.30 (1H, t, J=7.7 Hz), 7.45 (1H, t, J=1.6 Hz), 7.49 (1H, dt, J=7.6, 1.6 Hz), 7.90 (1H, s). ¹³C NMR (CDCl₃, 100 MHz): δ 13.9, 27.8, 47.0, 83.2, 121.5, 122.0, 128.9, 129.1, 130.4, 132.8, 132.9, 134.6, 136.5, 146.1, 156.3, 161.6, 166.3.

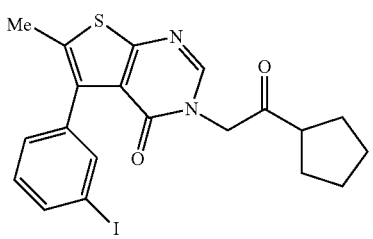

1622-64

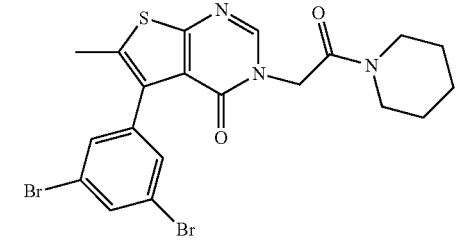

1622-69

1622-64:

¹H NMR (CDCl₃, 400 MHz): δ 1.51-1.73 (4H, m), 1.75-1.96 (4H, m), 2.36 (3H, s), 2.99 (1H, quint, J=8.0 Hz), 4.78 (2H, s), 7.20-7.31 (2H, m), 7.43 (1H, s), 7.48 (1H, d, J=7.7 Hz), 7.79 (1H, s). ¹³C NMR (CDCl₃, 100 MHz): δ 13.9, 25.9, 28.7, 49.1, 52.6, 121.6, 122.1, 128.9, 129.1, 130.5, 132.8, 132.9, 134.6, 136.6, 146.2, 156.3, 161.8, 204.6.

1622-69:

¹H NMR (CDCl₃, 400 MHz): δ 1.52-1.71 (6H, m), 2.35 (3H, s), 3.42-3.58 (4H, m), 4.76 (2H, s), 7.38 (2H, d, J=1.7 Hz), 7.65 (1H, dd, J=1.9, 1.7 Hz), 7.94 (1H, s). ¹³C NMR (CDCl₃, 100 MHz): δ 13.9, 24.2, 25.2, 26.1, 43.4, 45.4, 45.9, 121.8, 121.9, 131.3, 131.8, 132.8, 135.0, 138.1, 147.0, 156.4, 161.9, 163.8.

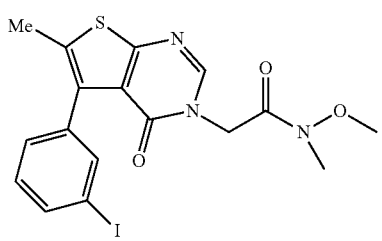

1622-65

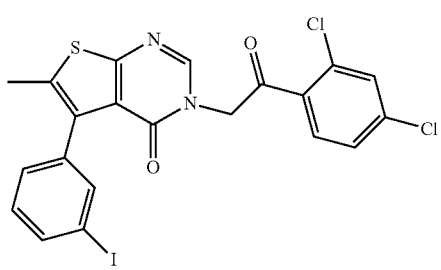

1622-70

1622-65:

¹H NMR (CDCl₃, 400 MHz): δ 2.35 (3H, s), 3.20 (3H, s), 3.78 (3H, s), 4.85 (2H, s), 7.21-7.31 (2H, m), 7.44 (1H, s), 7.48 (1H, d, J=7.3 Hz), 7.90 (1H, s). ¹³C NMR (CDCl₃, 100 MHz): δ 13.9, 32.4, 45.8, 61.6, 121.6, 122.1, 129.0, 129.1, 130.4, 132.8, 132.9, 134.5, 136.7, 146.7, 156.7, 161.9, 166.9.

1622-70:

¹H NMR (CDCl₃, 400 MHz): δ 2.38 (3H, s), 5.21 (2H, s), 7.22 (1H, dt, J=7.6, 1.4 Hz), 7.27 (1H, t, J=7.7 Hz), 7.35 (1H, dd, J=8.4, 1.9 Hz), 7.42 (1H, dd, J=1.9, 1.6 Hz), 7.4 (1H, d, J=1.9 Hz), 7.48 (1H, ddd, J=7.7, 1.8, 1.4 Hz), 7.70 (1H, d, J=8.4 Hz), 7.95 (1H, s). ¹³C NMR (CDCl₃, 100 MHz): δ 13.9, 54.4, 121.6, 127.7, 128.8, 129.1, 130.4, 130.5, 131.8, 132.5, 132.8, 132.9, 133.9, 134.9, 136.4, 139.1, 146.1, 156.3, 162.0, 192.8.

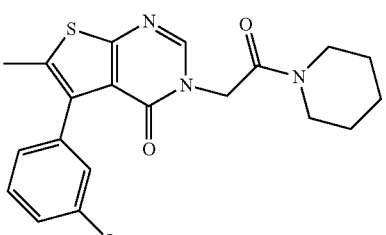

1622-68

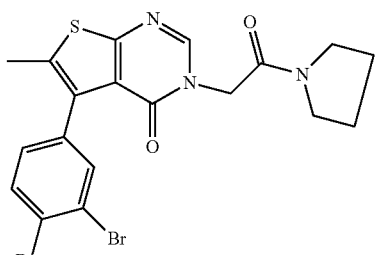

1622-71

1622-68:

¹H NMR (CDCl₃, 400 MHz): δ 1.50-1.71 (6H, m), 2.35 (3H, s), 3.43 (2H, t, J=7.2 Hz), 3.53 (2H, t, J=7.5 Hz), 4.76 (2H, s), 7.22-7.31 (2H, m), 7.44 (1H, t, J=1.8, 1.6 Hz), 7.48 (1H, dt, J=7.5, 1.8, 1.6 Hz), 7.93 (1H, s). ¹³C NMR (CDCl₃, 100 MHz): δ 13.8, 24.1, 25.1, 26.1, 43.3, 45.4, 45.8, 121.5, 121.9, 128.9, 129.0, 130.3, 132.7, 132.8, 134.3, 136.7, 146.8, 156.5, 161.8, 163.9.

1622-71:

¹H NMR (CDCl₃, 400 MHz): δ 1.86 (2H, quint, J=6.9 Hz), 1.99 (2H, quint, J=6.8 Hz), 2.35 (3H, s), 3.47 (2H, t, J=6.9 Hz), 3.52 (2H, t, J=6.8 Hz), 4.65 (2H, s), 7.12 (1H, dd, J=8.2, 1.9 Hz), 7.55 (1H, d, J=1.9 Hz), 7.63 (1H, d, J=8.2 Hz), 7.98 (1H, s). ¹³C NMR (CDCl₃, 100 MHz): δ 13.9, 24.0, 26.0, 45.8, 46.2, 46.4, 121.8, 123.9, 130.5, 131.7, 132.7, 134.7, 135.0, 135.4, 146.9, 156.6, 162.0, 163.9.

1622-72

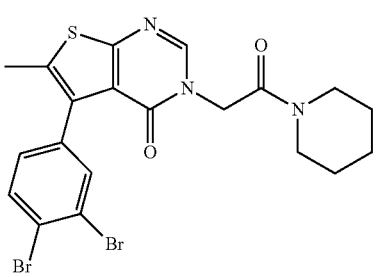

1622-72:

¹H NMR (CDCl₃, 400 MHz): δ 1.48-1.72 (6H, m), 2.35 (3H, s), 3.42 (2H, t, J=5.5 Hz), 3.52 (2H, t, J=5.5 Hz), 4.74 (2H, s), 7.11 (1H, dd, J=8.2, 2.0 Hz), 7.55 (1H, d, J=2.0 Hz), 7.63 (1H, d, J=8.2 Hz), 7.93 (1H, s). ¹³C NMR (CDCl₃, 100 MHz): δ 13.9, 24.2, 25.2, 26.2, 43.4, 45.5, 45.9, 121.8, 123.8, 123.9, 130.5, 131.7, 132.7, 134.6, 135.0, 135.4, 146.9, 156.6, 162.0, 163.8.

1622-73

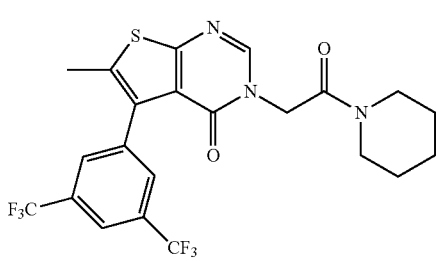

1622-73:

¹H NMR (CDCl₃, 400 MHz): δ 1.49-1.75 (6H, m), 2.38 (3H, s), 3.40-3.51 (4H, m), 4.75 (2H, s), 7.77 (2H, s), 7.85 (1H, s), 7.97 (1H, s). ¹³C NMR (CDCl₃, 100 MHz): δ 13.8, 24.2, 25.2, 26.2, 43.5, 45.4, 46.1, 121.2, 121.6, 123.3 (q, J=272 Hz), 130.6, 130.7 (q, J=33 Hz), 131.2, 135.4, 136.5, 147.2, 156.6, 162.2, 163.8.

Exemplary compounds according to Formula II include the following compounds:

1622-2040

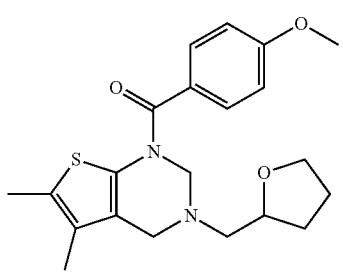

1622-2039

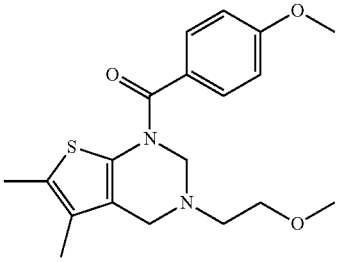

Example 2: N-Methyl-D-Aspartate Receptor Positive Allosteric Modulators and their Effects in Hippocampal CA1 Neurons A series of positive modulators of NMDA-Rs have been identified. Evaluation of this series revealed that these compounds can potentiate GluN2B-containing receptors by 2 to 4 fold (EC50 4-15 μM) in addition to potentiating those containing GluN2C and GluN2D by 2 to >4 fold. Compound 1622 (FIG. 5A) enhanced glutamate potency (1.7-fold). This series potentiates NMDA-Rs by increasing the time the channel spends in the open conformation (1622 30 μM, 2 fold increase in $NP_o$, n=3). In rapid solution exchange electrophysiology experiments, 1622-35 prolonged the deactivation of NMDA-Rs roughly 3-fold, by enhanced glutamate potency. In hippocampal CA1 neurons, which express GluN2A and GluN2B, 1622-35 prolonged the time course of excitatory post synaptic currents (control 280±30 ms, 10 μM 1622-35 970±220 ms, n=4) as well as increased the total charge transfer of these events (2.3 times greater than control).

Example 3: Two-Electrode Voltage-Clamp Recordings from *X. Laevis*

*Xenopus laevis* oocytes were injected with cRNA encoding the NMDA receptor subunits. Two to seven days after injection, two-electrode voltage-clamp recordings were performed. Extracellular solutions were made from a solutions containing (in mM) 90 NaCl, 3 KCl, 10 HEPES, 0.5 BaCl₂, 0.01 EDTA (pH 7.4 with NaOH). Voltage and current electrodes were filled with 0.3 M and 3.0 M KCl, respectively.

Potency was determined by adding increasing concentrations of test compound to saturating concentrations of glutamate (100 μM) and glycine (30 μM), and the response amplitude measured. The response in the presence of each concentration of test compound plus agonists was expressed as a percent of the response in the absence of test compound.

These data were fitted to the standard Hill equation to determine the concentration at which the response was half maximal ($EC_{50}$ for potentiators, $IC_{50}$ for inhibitors). Data are shown in Tables 1-6 below.

TABLE 1

[Structure: thieno[2,3-d]pyrimidin-4(3H)-one with R³ at position 6, R² at position 5, and N3 substituted with -CH₂-C(=O)-pyrrolidinyl]

| R² | R³ | $I_{10 \mu M}/I_{CONTROL}$ (mean ± SEM, %) | | | EC$_{50}$ (maximal potentiation) (μM, %) | | |
| --- | --- | --- | --- | --- | --- | --- | --- |
|  |  | Glu N2B | Glu N2C | Glu N2D | Glu N2B | Glu N2C | Glu N2D |
| 4-Cl—Ph | Me |  |  |  | 11 (223) | 15 (347) | 23 (381) |
| Me | Me |  |  |  | — | — | — |
| H | H |  |  |  | — | — | — |
| 4-F—Ph | Me |  |  |  | 54 (213) | 81 (448) | 124 (428) |
| 3,4-Me—Ph | Me |  |  |  | 7.9 (192) | 27 (267) | 18 (229) |
| 4-Br—Ph | Me |  |  |  | 11.3 (163) | 60 (449) | 79 (400) |
| 4-Cl—Ph | H |  |  |  | 46 (314) | 76 (770) | 72 (512) |
| 4-OEt—Ph | Me |  |  |  | 15 (147) | 18 (186) | 18 (232) |
| 4-Me—Ph | H |  |  |  | 109 (226) | 207 (597) | 170 (560) |
| 4-Et—Ph | H |  |  |  | 39 (223) | 66 (417) | 58 (355) |
| 2-thiophene | H |  |  |  | — | — | — |
| Me | Ph |  |  |  | — | — | — |
| Ph | H |  |  |  | NE | NE | NE |
| 4-I—Ph | H | 121 ± 5.7 | 110 ± 2.1 | 101 ± 1.8 | 75 (262) | 89 (369) | 45 (206) |
| 4-$^i$Pr—Ph | H | 121 ± 6.9 | 100 ± 2.5 | 98 ± 1.4 | 33 (174) | — | — |
| 4-MeS—Ph | H | 102 ± 4.6 | 99 ± 2.5 | 96 ± 2.6 | — | — | — |
| 3-Cl—Ph | Me | 170 ± 4.7 | 211 ± 14.7 | 190 ± 6.3 | 16 (301) | 36 (877) | 37 (830) |
| 3-Br—Ph | Me | 172 ± 8.7 | 241 ± 19.7 | 239 ± 11.5 | 11 (266) | 17 (568) | 21 (687) |
| 4-BnO—Ph | Me | 118 ± 5.2 | 135 ± 5.4 | 131 ± 3.7 | 11 (147) | 35 (392) | 25 (291) |
| 4-N₃—Ph | H | 134 ± 6.7 | 166 ± 7.2 | 147 ± 6.3 | 88 (353) | 102 (918) | 134 (730) |
| 4-N₃—Ph | Me | 135 ± 5.5 | 146 ± 6.4 | 128 ± 2.6 | 54 (304) | 54 (485) | 50 (426) |
| 4-NH₂—Ph | Me | 104 ± 1.7 | 116 ± 4.5 | 103 ± 2.2 | — | — | — |
| 3-N₃—Ph | Me | 176 ± 8.1 | 264 ± 17.7 | 175 ± 9.4 | 23.8 (295) | 10 (613) | 10 (592) |
| 4-OH—Ph | Me | 82 ± 1.0 | 98 ± 2.3 | 99 ± 2.5 | — | — | — |
| 3-I—Ph | Me | 246 ± 14.9 | 401 ± 36.4 | 364 ± 31.6 | 3.7 (249) | 7.6 (622) | 15 (1068) |
| 3-CN—Ph | Me | 147 ± 4.1 | 190 ± 4.2 | 177 ± 6.2 |  |  |  |
| Ph | Me | 115 ± 5.4 | 120 ± 3.7 | 148 ± 9.1 | 15 (153) | 14 (168) | 12 (262) |
| 3-CF₃—Ph | Me | 211 ± 11.3 | 368 ± 29.0 | 480 ± 74.3 | 6 (282) | 13 (748) | 25 (1735) |
| 3-1,2,4 triazolyl-Ph | Me | 110 ± 2.6 | 113 ± 5.8 | 108 ± 6.2 | 293 (402) | 44 (308) | 108 (239) |
| 3-N-imidazolyl-Ph | Me | 120 ± 5.8 | 112 ± 1.3 | 99 ± 3.4 | 102 (261) | 191 (453) | 80 (207) |
| 3,5-Br—Ph | Me | 156 ± 5.2 | 195 ± 6.9 | 230 ± 13.5 | 1.08 (143) | 2.2 (195) | 3.86 (202) |
| 3,5-F—Ph | Me | 107 ± 2.7 | 114 ± 0.9 | 116 ± 4.4 | 96 (229) | 132 (458) | 204 (748) |
| 3-NO₂—Ph | Me | 185 ± 4.8 | 321 ± 13.6 | 253 ± 13.3 | 12 (304) | 36 (1483) | 60 (1860) |
| 3,5-CF₃—Ph | Me | 101 ± 4.5 | 115 ± 5.5 | 103 ± 1.1 |  |  |  |
| 3,5-I—Ph | Me | 152 ± 8.8 | 167 ± 9.6 | 151 ± 6.3 | 20 (259) | 35 (493) | 32 (432) |
| 3,4-(CH₂)₃—Ph | Me | 176 ± 6.2 | 185 ± 11.4 | 165 ± 3.4 | 11.5 (275) | 26 (475) | 48 (580) |
| 2-CF₃—Ph | Me | 93 ± 2.0 | 95 ± 2.1 | 94 ± 1.4 | — | — | — |
| 3,4-Br—Ph | Me | 188 ± 9.3 | 281 ± 17.7 | 292 ± 13.7 | 5.2 (223) | 13 (561) | 30 (1205) |

TABLE 2

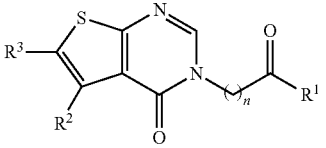

| n | R² | R³ | R¹ | $I_{10} \mu M/I_{CONTROL}$ (mean ± SEM, %) | | | $IC_{50}$ (maximal potentiation) ($\mu M$, %) | | |
|---|---|---|---|---|---|---|---|---|---|
| | | | | Glu N2B | Glu N2C | Glu N2D | Glu N2B | Glu N2C | Glu N2D |
| 1 | 4-Cl—Ph | Me | —Npyrrolidine | | | | 11 (223) | 15 (347) | 23 (381) |
| 1 | 4-Cl—Ph | Me | —Nmorpholine | | | | — | — | — |
| 1 | 4-Cl—Ph | Me | —N(Et)₂ | | | | — | — | — |
| 1 | 4-Cl—Ph | Me | NH₂ | | | | — | — | — |
| 1 | 4-Cl—Ph | Me | —Npiperidine | | | | — | 136 (232) | 52 (163) |
| 1 | Me | Me | —Nazetidine | | | | — | — | — |
| 1 | 4-Cl—Ph | H | —N-2-azaindan | | | | — | — | — |
| 1 | 4-Cl—Ph | H | —N-2-pyrrolidinone | | | | — | — | — |
| 1 | Ph | H | —N-2-imidazolidinone | | | | — | — | — |
| 1 | 4-Me—Ph | H | —Nazetidine | | | | — | >100 | 57 (0) |
| 2 | 4-Me—Ph | H | —Npyrrolidine | | | | — | — | — |
| 1 | 4-F—Ph | H | —N-2-(2-thienyl)-pyrrolidine | | | | — | — | — |
| 1 | 4-Br—Ph | Me | —NHCH2COOEt | 96 ± 2.1 | 104 ± 2.5 | 104 ± 0.6 | — | — | — |
| 1 | 4-Br—Ph | Me | —N(Me)₂ | 92 ± 1.7 | 109 ± 3.1 | 105 ± 1.8 | — | — | — |
| 1 | 4-Br—Ph | Me | —Nproline methylester (S) | 109 ± 4.9 | 159 ± 9.5 | 147 ± 12.7 | — | — | — |
| 1 | 4-Cl—Ph | Me | —NHCH₂COOH | 87 ± 1.3 | 105 ± 3.7 | 93 ± 1.8 | — | — | — |
| 1 | 4-Cl—Ph | Me | —Nproline (S) | 89 ± 1.7 | 104 ± 2.3 | 97 ± 1.9 | — | — | — |
| 1 | 3-Cl—Ph | Me | OEt | 127 ± 4.6 | 141 ± 7.0 | 136 ± 3.0 | 17 (148) | 26 (390) | 16 (245) |
| 1 | 3-Cl—Ph | Me | OH | 93 ± 1.2 | 93 ± 1.4 | 89 ± 1.4 | — | — | — |
| 1 | 3-Cl—Ph | Me | SEt | 95 ± 0.9 | 95 ± 2.8 | 90 ± 1.3 | — | — | — |
| 2 | 3-Cl—Ph | Me | OEt | 107 ± 2.3 | 91 ± 2.5 | 97 ± 1.6 | — | — | — |
| 1 | 3-Cl—Ph | Me | StBu | 92 ± 4.6 | 87 ± 4.0 | 73 ± 2.6 | — | — | — |
| 2 | 3-Cl—Ph | Me | OH | 99 ± 0.6 | 89 ± 6.2 | 97 ± 1.1 | — | — | — |
| 2 | 3-Cl—Ph | Me | —Npyrrolidine | 95 ± 1.7 | 99 ± 5.0 | 90 ± 1.7 | — | — | — |
| 1 | 3-Cl—Ph | Me | 2-thiophene | 133 ± 3.9 | 125 ± 2.8 | 137 ± 6.3 | 14 (207) | 19 (293) | 15 (224) |
| 2 | 3-Cl—Ph | Me | OPh | 104 ± 3.6 | 91 ± 1.1 | 88 ± 2.4 | — | — | — |
| 1 | 3-Cl—Ph | Me | OPh | 96 ± 2.6 | 110 ± 5.9 | 89 ± 1.6 | — | — | — |
| 1 | 3-I—Ph | Me | 2-thiophene | 129 ± 4.5 | 180 ± 10.7 | 177 ± 7.0 | 7.7 (147) | 9.3 (255) | 11 (262) |
| 1 | 3-I—Ph | Me | Ph | 139 ± 3.9 | 161 ± 10.9 | 133 ± 3.1 | 7.9 (169) | 15 (273) | 41 (305) |
| 1 | 3-I—Ph | Me | 4-OMe—Ph | 84 ± 5.2 | 94 ± 1.94 | 94 ± 1.1 | — | — | — |
| 1 | 3-I—Ph | Me | 3-OMe—Ph | 107 ± 3.0 | 107 ± 4.9 | 99 ± 4.3 | — | — | — |
| 1 | 3-I—Ph | Me | OtBu | 87 ± 3.9 | 101 ± 6.8 | 94 ± 4.3 | — | — | — |
| 1 | 3-I—Ph | Me | -cyclopentyl | — | 166 ± 9.5 | 133 ± 3.0 | — | 9.4 (225) | 14 (191) |
| 1 | 3-I—Ph | Me | —N(OMe)Me | — | 109 ± 4.9 | 119 ± 8.9 | — | — | — |
| 1 | 3-I—Ph | Me | —Npiperidine | — | 145 ± 11.4 | 124 ± 4.8 | — | — | — |
| 1 | 3,5-Br—Ph | Me | —Npiperidine | — | 232 ± 14.4 | 179 ± 10.1 | — | 4.3 (233) | — |
| 1 | 3-I—Ph | Me | 2,4-Cl—Ph | — | 96 ± 4.8 | 93 ± 1.8 | — | — | — |
| 1 | 3,4-Br—Ph | Me | —Npiperidine | — | 168 ± 13.9 | 143 ± 3.2 | — | 15 (300) | 94 (600) |
| 1 | 3,5-CF₃—Ph | Me | —Npiperidine | | | | — | 1.4 (155) | — |

TABLE 3

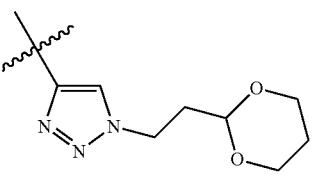 [SMILES: *c1cn(CCC2OCCCO2)nn1]

| R | $I_{10}$ µM/$I_{CONTROL}$ (mean ± SEM, %) | | | IC$_{50}$ (maximal potentiation) (µM, %) | | |
|---|---|---|---|---|---|---|
| | Glu N2B | Glu N2C | Glu N2D | Glu N2B | Glu N2C | Glu N2D |
| —C≡CH | 116 ± 4.0 | 98 ± 7.9 | 98 ± 4.3 | — | — | — |
| (triazole-dioxane, 1,4-substituted) | 89 ± 2.5 | 88 ± 0.5 | 88 ± 3.4 | — | — | — |
| (triazole-dioxane, 1,5-substituted) | 89 ± 2.5 | 92 ± 0.8 | 91 ± 1.3 | — | — | — |
| (triazole-OMe ethyl) | 99 ± 1.9 | 93 ± 2.2 | 84 ± 3.4 | — | — | — |

TABLE 4

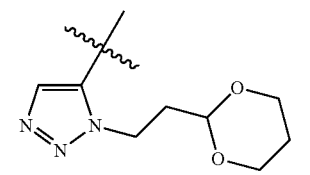 [SMILES: *c1cnnn1CCC1OCCCO1]

| R | $I_{10}$ µM/$I_{CONTROL}$ (mean ± SEM, %) | | | IC$_{50}$ (maximal potentiation) (µM, %) | | |
|---|---|---|---|---|---|---|
| | Glu N2B | Glu N2C | Glu N2D | Glu N2B | Glu N2C | Glu N2D |
| 4-Br | 92 ± 1.6 | 92 ± 1.2 | 94 ± 0.4 | — | — | — |
| 3-OMe | 97 ± 1.2 | 129 ± 4.4 | 122 ± 4.0 | — | — | — |
| 4-OMe | 95 ± 1.9 | 201 ± 6.5 | 152 ± 2.5 | — | — | — |
| H | 101 ± 1.7 | 105 ± 1.6 | 100 ± 0.9 | — | — | — |
| 4-Cl | 99 ± 6.3 | 198 ± 13.5 | 197 ± 8.6 | — | — | — |

TABLE 5

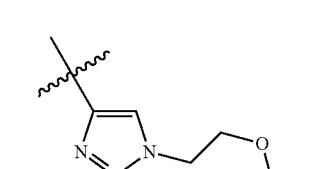

| R | $I_{10}$ µM/$I_{CONTROL}$ (mean ± SEM, %) | | | IC$_{50}$ (maximal potentiation) (µM, %) | | |
|---|---|---|---|---|---|---|
| | Glu N2B | Glu N2C | Glu N2D | Glu N2B | Glu N2C | Glu N2D |
| 4-NO$_2$ | 94 ± 1.3 | 93 ± 2.0 | 97 ± 1.1 | — | — | — |
| 2,4-OMe | 95 ± 1.8 | 94 ± 1.4 | 90 ± 0.7 | — | — | — |
| 2,4-Cl | 91 ± 3.6 | 106 ± 4.4 | 97 ± 1.8 | — | — | — |

TABLE 6

| | IC$_{50}$ (μM) | | |
|---|---|---|---|
| | Glu N2B | Glu N2C | Glu N2D |
| (structure) | 86% response at 100 μM | 46 | 109 |
| (structure) | 92% response at 100 μM | 6 | 35 |

Figure 1B:
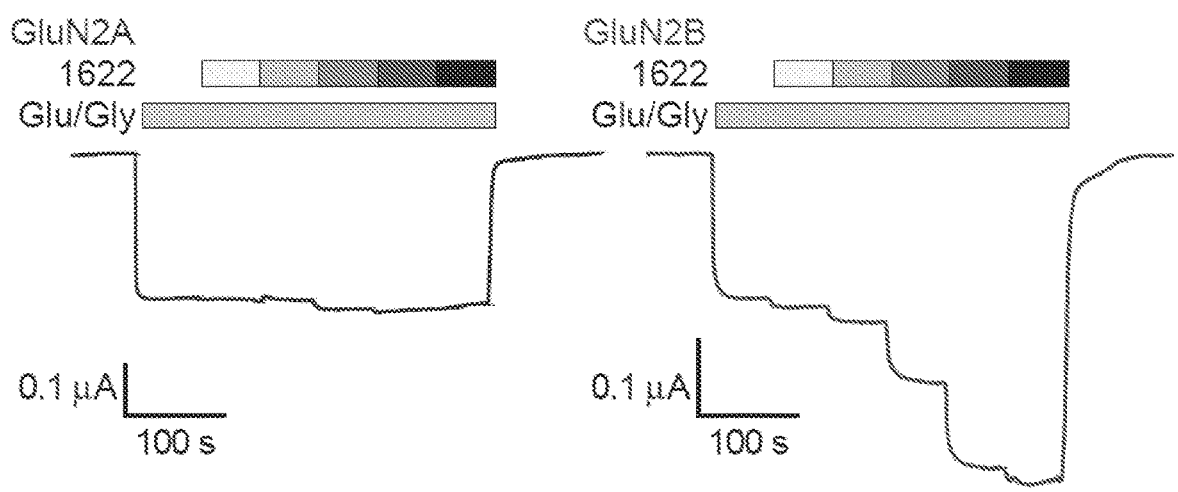
FIG. 1B shows traces of a concentration-response experiment (1-100 μM) demonstrating the effects of 1622 on GluN2A and GluN2B expressing oocytes.

Representative traces of a concentration-response experiment (1-100 μM) demonstrating the effects of 1622 (FIG. 1A) on GluN2A and GluN2B expressing oocytes are shown in FIG. 1B. The data indicates that 1622 is a positive NMDA receptor modulator that potentiates receptors activated by maximally effective concentrations of glutamate and glycine and that contain GluN2B but not GluN2A.

Example 4: Rapid Solution on Exchange Experiments

HEK293 cells were transfected used the CaPO$_4$ method. Cells were patched 1-3 days later and lifted into the flow from a theta tube perfusion. A piezoelectric translator was used to rapidly exchange the solution surrounding the lifted cell, full solution on exchange was achieved in less than 5 ms. NMDA receptor currents were activated using 100 μM glutamate and 30 μM glycine. Patch clamp recording of an excised outside-out patch of a GluN1/GluN2B expressing HEK293 cells in the absence and presence of 30 μM 1622-35 indicate increases in GluN1/GluN2 channel function and slows deactivation. Summary data shown in Table 7 below.

TABLE 7

| | Control | 1622-35 (10 μM) | Fold Increase | N |
|---|---|---|---|---|
| Peak Amplitude (pA) | 628 ± 237 | 1694 ± 417* | 3.4 ± 0.6 | 4 |
| Decay Time Constant (ms) | 681 ± 142 | 3037 ± 166* | 5.7 ± 1.9 | 4 |

Example 5: Slice Recordings

Coronal hippocampal brain slices were made from mice (p7-14) using a vibrotome. During slice cutting and recovery, the slices were bathed in an artificial cerebral spinal fluid (slicing aCSF—containing, in mM: 75 NaCl, 2.5 KCl, 1.25 NaH$_2$PO$_4$, 25 NaHCO$_3$, 5 MgCl$_2$ or MgSO4, 0.5 CaCl2, 20 Glucose, 70 Sucrose). Whole cell recordings were made using a different aCSF (recording aCSF—containing, in mM: 130 NaCl, 2.5 KCl, 1.25 NaH$_2$PO$_4$, 25 NaHCO$_3$, 0.1 MgCl$_2$ or MgSO$_4$, 2.5 CaCl$_2$, 20 Glucose), and using a CsGlu internal solution containing, following (in mM): 110 d-gluconic acid, 110 CsOH, 30 CsCl, 5 HEPES, 4 NaCl, 0.5 CaCl$_2$, 2 MgCl$_2$, 5 BAPTA, 2 Na2ATP, and 0.3 NaGTP (pH 7.35). Experiments indicate that 1622-35 potentiates only the NMDA component of the sEPSCs in hippocampal pyramidal neurons. 1622-35 enhances the NMDA components of CA1 EPSPs during theta burst stimulation indicating 1622 will enhance synaptic plasticity.

The compounds and methods of the appended claims are not limited in scope by the specific compounds and methods described herein, which are intended as illustrations of a few aspects of the claims and any compounds and methods that are functionally equivalent are within the scope of this disclosure. Various modifications of the compounds and methods in addition to those shown and described herein are intended to fall within the scope of the appended claims. Further, while only certain representative compounds, methods, and aspects of these compounds and methods are specifically described, other compounds and methods are intended to fall within the scope of the appended claims. Thus, a combination of steps, elements, components, or constituents can be explicitly mentioned herein; however, all other combinations of steps, elements, components, and constituents are included, even though not explicitly stated.

What is claimed is:
1. A compound of Formula I,

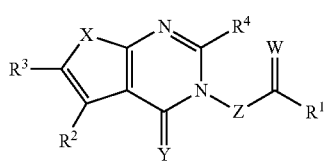

Formula I or a salt thereof, wherein:
X is S;
Y is S, O, or NH;
Z is S, O, NH, or CH$_2$;
W is O, S, or NH;
R$^1$ is pyrrolidin-1-yl or azetidin-1-yl, substituted with one or more, the same or different, R$^5$,
R$^2$ is phenyl or six-membered heteroaryl, substituted with one or more, the same or different, R$^5$, having at least one R$^5$ substituent at the 3- or 5-position relative to the ring atom of R$^2$ that connects to the rest of Formula I, wherein the ring atom of R$^2$ that connects to the rest of Formula I corresponds to the 1-position;
R$^3$ is hydrogen, alkyl, halogen, cyano, hydroxy, amino, mercapto, formyl, carboxy, carbamoyl, alkoxy, alkanoyl, alkylthio, alkylamino, aminoalkyl, (alkyl)$_2$ amino, alkylsulfinyl, alkylsulfonyl, arylsulfonyl, carbocyclyl, aryl, or heterocyclyl, wherein R$^3$ is optionally substituted with one or more, the same or different, R$^5$;
R$^4$ is hydrogen, alkyl, halogen, cyano, hydroxy, amino, mercapto, formyl, carboxy, carbamoyl, alkoxy, alkanoyl, alkylthio, alkylamino, aminoalkyl, (alkyl)$_2$ amino, alkylsulfinyl, alkylsulfonyl, arylsulfonyl, carbocyclyl, aryl, or heterocyclyl, wherein R$^4$ is optionally substituted with one or more, the same or different, R$^5$;

$R^5$ is alkyl, halogen, nitro, cyano, hydroxy, amino, mercapto, formyl, carboxy, carbamoyl, alkoxy, alkanoyl, alkylthio, alkylamino, (alkyl)$_2$amino, alkylsulfinyl, alkyl sulfonyl, arylsulfonyl, carbocyclyl, aryl, or heterocyclyl, wherein $R^5$ is optionally substituted with one or more, the same or different, $R^6$;

$R^6$ is alkyl, halogen, nitro, cyano, hydroxy, amino, mercapto, formyl, carboxy, carbamoyl, alkoxy, alkanoyl, alkylthio, alkylamino, (alkyl)$_2$amino, alkylsulfinyl, alkyl sulfonyl, arylsulfonyl, carbocyclyl, aryl, or heterocyclyl, wherein $R^6$ is optionally substituted with one or more, the same or different, $R^7$; and $R^7$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethyl carbamoyl, N,N-dimethylcarbamoyl, N,N-diethyl carbamoyl, N-methyl-N-ethyl carb amoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

2. The compound of claim 1, wherein $R^3$ is hydrogen, alkyl, or methyl, $R^4$ is hydrogen, Z is CH$_2$, and W is O.

3. The compound of claim 1, wherein $R^1$ is pyrrolidin-1-yl substituted with one or more, the same or different, $R^5$.

4. A pharmaceutical composition comprising a compound of claim 1 and a pharmaceutically acceptable excipient.

5. The pharmaceutical composition of claim 4, in the form of a tablet, capsule, pill, gel, solid formulation comprising a saccharide, polysaccharide, or fatty acid, a pH buffered solution, or a solution containing an alcohol or oil.

6. The compound of claim 1, wherein $R^2$ has an $R^5$ substituent at the 4-position relative to the ring atom in $R^2$ that connects to the rest of Formula I.

7. The compound of claim 6, wherein $R^2$ is phenyl substituted with one or more, the same or different, $R^5$, having at least one $R^5$ substituent at the 3- or 5-position relative to the ring atom of $R^2$ that connects to the rest of Formula I and an $R^5$ substituent at the 4-position relative to the ring atom in $R^2$ that connects to the rest of Formula I.

8. The compound of claim 1, wherein $R^2$ is phenyl substituted with one or more, the same or different, $R^5$, having at least one $R^5$ substituent at the 3- or 5-position relative to the ring atom of $R^2$ that connects to the rest of Formula I.

9. The compound of claim 1, wherein $R_1$ is azetidin-1-yl substituted with one or more, the same or different, $R^5$.

10. A compound of Formula IB,

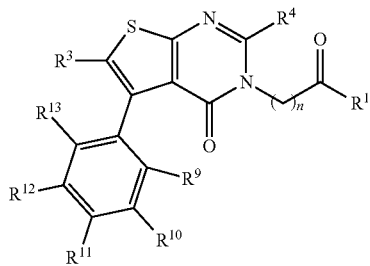

Formula IB or a salt thereof, wherein:

n is 1 or 2;

$R^1$ is 5-membered heterocyclyl or azetidin-1-yl, optionally substituted with one or more, the same or different, $R^5$;

$R^3$ is hydrogen, alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^3$ is optionally substituted with one or more, the same or different, $R^5$;

$R^4$ is hydrogen, alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^4$ is optionally substituted with one or more, the same or different, $R^5$;

$R^5$ is alkyl, halogen, nitro, cyano, hydroxy, amino, mercapto, formyl, carboxy, carbamoyl, alkoxy, alkanoyl, alkylthio, alkylamino, (alkyl)$_2$amino, alkylsulfinyl, alkyl sulfonyl, arylsulfonyl, carbocyclyl, aryl, or heterocyclyl, wherein $R^5$ is optionally substituted with one or more, the same or different, $R^6$ ;

$R^6$ is alkyl, halogen, nitro, cyano, hydroxy, amino, mercapto, formyl, carboxy, carbamoyl, alkoxy, alkanoyl, alkylthio, alkylamino, (alkyl)$_2$amino, alkylsulfinyl, alkyl sulfonyl, arylsulfonyl, carbocyclyl, aryl, or heterocyclyl, wherein $R^6$ is optionally substituted with one or more, the same or different, $R^7$ ;

$R^7$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethyl sulfonyl, methoxycarbonyl, ethoxycarbonyl, N-m ethyl sulfamoyl, N-ethyl sulfamoyl, N,N-dimethylsulfamoyl, N,N-diethylsulfamoyl, N-methyl-N-ethylsulfamoyl, carbocyclyl, aryl, or heterocyclyl;

$R^9$, $R^{11}$, $R^{12}$, and $R^{13}$ are each individually and independently selected from the group consisting of hydrogen, alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, and heterocyclyl, wherein $R^9$, $R^{11}$, $R^{12}$, and $R^{13}$ , are, each individually and independently, optionally substituted with one or more, the same or different, $R^{15}$;

$R^{10}$ is selected from the group consisting of halogen, cyano, amino, mercapto, formyl, carboxy, carbamoyl, alkanoyl, alkylthio, alkylamino, aminoalkyl, (alkyl)$_2$amino, alkylsulfinyl, alkyl sulfonyl, aryl sulfonyl, carbocyclyl, aryl, and heterocyclyl, wherein $R^{10}$ is optionally substituted with one or more, the same or different, $R^{15}$;

$R^{15}$ is alkyl, halogen, nitro, cyano, hydroxy, amino, mercapto, formyl, carboxy, carbamoyl, alkoxy, alkanoyl, alkylthio, alkylamino, (alkyl)$_2$amino, alkyl sulfinyl, alkyl sulfonyl, arylsulfonyl, carbocyclyl, aryl, or heterocyclyl, wherein $R^{15}$ is optionally substituted with one or more, the same or different, $R^6$;

$R^{16}$ is alkyl, halogen, nitro, cyano, hydroxy, amino, mercapto, formyl, carboxy, carbamoyl, alkoxy, alkanoyl, alkylthio, alkylamino, (alkyl)2amino, alkyl sulfinyl, alkyl sulfonyl, arylsulfonyl, carbocyclyl, aryl, or heterocyclyl, wherein $R^{16}$ is optionally substituted with one or more, the same or different, $R^{17}$; and $R^{17}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methyl carb am oyl, N-ethyl carb am oyl, N,N-dimethyl carb amoyl, N,N-diethyl carbamoyl, N-methyl-N-ethyl carbamoyl, methylthio, ethylthio, methylsulfinyl, ethylsulfinyl, mesyl, ethylsulfonyl, methoxycarbonyl, ethoxycarbonyl, N-methyl sulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

11. The compound of claim 10, wherein the $R^1$ is 5-membered heterocyclyl, optionally substituted with one or more, the same or different, $R^5$.

12. The compound of claim 11, wherein the $R^1$ is pyrrolidin-1-yl, optionally substituted with one or more, the same or different, $R^5$.

13. The compound of claim 10, wherein the $R^1$ is azetidin-1-yl, optionally substituted with one or more, the same or different, $R^5$.

14. The compound of claim 10, wherein $R^{10}$ is halogen.

15. The compound of claim 10, wherein $R^{11}$ is halogen.

16. The compound of claim 10, wherein $R^9$ is hydrogen.

17. The compound of claim 10, wherein $R^{12}$ is hydrogen.

18. The compound of claim 10, wherein $R^{13}$ is hydrogen.

19. A compound of Formula ID,

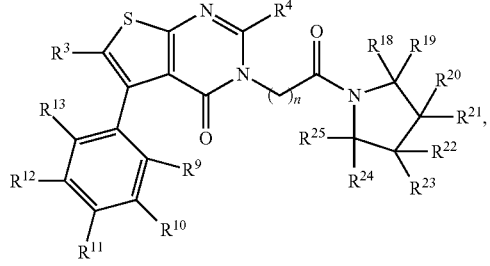

Formula ID or a salt thereof, wherein:

n is 1 or 2;

$R^3$ is hydrogen, alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl. alkylsulfonyl, arylsulfonyl, carbocyclyl, aryl, or heterocyclyl, wherein $R^3$ is optionally substituted with one or more, the same or different, $R^5$;

$R^4$ is hydrogen, alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, or heterocyclyl, wherein $R^4$ is optionally substituted with one or more, the same or different, $R^5$;

$R^5$ is alkyl, halogen, nitro, cyano, hydroxy, amino, mercapto, formyl, carboxy, carbamoyl, alkoxy, alkanoyl, alkylthio, alkylamino, (alkyl)$_2$amino, alkylsulfinyl, alkylsulfonyl, arylsulfonyl, carbocyclyl, aryl, or heterocyclyl, wherein $R^5$ is optionally substituted with one or more, the same or different, $R^6$.

$R^6$ is alkyl, halogen, nitro, cyano, hydroxy, amino, mercapto, formyl, carboxy, carbamoyl, alkoxy, alkanoyl, alkylthio, alkylamino, (alkyl)$_2$amino, alkylsulfinyl, alkylsulfonyl, arylsulfonyl, carbocyclyl, aryl, or heterocyclyl, wherein $R^6$ is optionally substituted with one or more, the same or different, $R^7$;

$R^7$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N, N-dimethylsulfamoyl, N,N-diethylsulfamoyl, N-methyl-N-ethylsulfamoyl, carbocyclyl, aryl, or heterocyclyl;

$R^9$, $R^{11}$, $R^{12}$, and $R^{13}$ are each individually and independently selected from the group consisting of hydrogen, alkyl, halogen, cyano, hydroxy, amino, mercapto, formyl, carboxy, carbamoyl, alkoxy, alkanoyl, alkylthio, alkylamino, aminoalkyl, (alkyl)$_2$amino, alkylsulfinyl, alkylsulfonyl, arylsulfonyl, carbocyclyl, aryl, and heterocyclyl, wherein $R^9$, $R^{11}$, $R^{12}$, and $R^{13}$, are, each individually and independently, optionally substituted with one or more, the same or different, $R^{15}$;

$R^{10}$ is selected from the group consisting of halogen, cyano, amino, mercapto, formyl, carboxy, carbamoyl, alkanoyl, alkylthio, alkylamino, aminoalkyl, (alkyl)$_2$amino, alkylsulfinyl, alkylsulfonyl, arylsulfonyl, carbocyclyl, aryl, and heterocyclyl, wherein $R^{10}$ is optionally substituted with one or more, the same or different, $R^{15}$;

$R^{15}$ is alkyl, halogen, nitro, cyano, hydroxy, amino, mercapto, formyl, carboxy, carbamoyl, alkoxy, alkanoyl, alkylthio, alkylamino, (alkyl)$_2$amino, alkylsulfinyl, alkylsulfonyl, arylsulfonyl, carbocyclyl, aryl, or heterocyclyl, wherein $R^{15}$ is optionally substituted with one or more, the same or different, $R^{16}$;

$R^{16}$ is alkyl, halogen, nitro, cyano, hydroxy, amino, mercapto, formyl, carboxy, carbamoyl, alkoxy, alkanoyl, alkylthio, alkylamino, (alkyl)$_2$amino, alkylsulfinyl, alkylsulfonyl, arylsulfonyl, carbocyclyl, aryl, or heterocyclyl, wherein $R^{16}$ is optionally substituted with one or more, the same or different, $R^{17}$, and $R^{17}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N, N-dimethylsulfamoyl, N,N-diethylsulfamoyl, N-methyl-N-ethylsulfamoyl, carbocyclyl, aryl, or heterocyclyl;

$R^{18}$, $R^{19}$, $R^{20}$, $R^{21}$, $R^{22}$, $R^{23}$, $R^{24}$, and $R^{25}$, are each individually and independently selected from the group consisting of hydrogen, alkyl, halogen, cyano, hydroxy, amino, mercapto, formyl, carboxy, carbamoyl, alkoxy, alkanoyl, alkylthio, alkylamino, alkylamino, (alkyl)$_2$amino, alkylsulfinyl, alkylsulfonyl, arylsulfonyl, carbocyclyl, aryl, and heterocyclyl, wherein $R^{18}$, $R^{19}$, $R^{20}$, $R^{21}$, $R^{22}$, $R^{23}$, $R^{24}$, and $R^{25}$, are, each individually and independently, optionally substituted with one or more, the same or different, $R^{26}$;

$R^{26}$ is alkyl, halogen, nitro, cyano, hydroxy, amino, mercapto, formyl, carboxy, carbamoyl, alkoxy, alkanoyl, alkylthio, alkylamino, (alkyl)²amino, alkylsulfinyl, alkyl sulfonyl, arylsulfonyl, carbocyclyl, aryl, or heterocyclyl, wherein $R^{26}$ is optionally substituted with one or more, the same or different, $R^{27}$;

and $R^{27}$ is halogen, nitro, cyano, hydroxy, amino, mercapto, formyl, carboxy, carbamoyl, alkoxy, alkanoyl, alkylthio, alkylamino, (alkyl)2amino, alkylsulfinyl, alkyl sulfonyl, arylsulfonyl, carbocyclyl, aryl, or heterocyclyl, wherein $R^{27}$ is optionally substituted with one or more, the same or different, $R^{28}$ ; and and $R^{27}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

20. A compound selected from the group consisting of:
5-(3-iodophenyl)-6-methyl-3-(2-oxo-2-(pyrrolidin-1-yl) ethyl)thieno[2,3-d]pyrimidin-4(3H)-one;
5-(3-chlorophenyl)-6-methyl-3-(2-oxo-2-(pyrrolidin-1-yl)ethyl)thieno[2,3-d]pyrimidin-4(3H)-one;
5-(3-bromophenyl)-6-methyl-3-(2-oxo-2-(pyrrolidin-1-yl)ethyl)thieno[2,3-d]pyrimidin-4(3H)-one;
5-(3-bromophenyl)-6-methyl-3-(2-oxo-2-(pyrrolidin-1-yl)ethyl)thieno[2,3-d]pyrimidin-4(3H)-one;
5-(3-trifluoromethylphenyl)-6-methyl-3-(2-oxo-2-(pyrrolidin-1-yl)ethyl)thieno[2,3-d]pyrimidin-4(3H)-one;
5-(3-nitrophenyl)-6-methyl-3-(2-oxo-2-(pyrrolidin-1-yl) ethyl)thieno[2,3-d]pyrimidin-4(3H)-one;
5-(3,5-dibromophenyl)-6-methyl-3-(2-oxo-2-(pyrrolidin-1-yl)ethyl)thieno[2,3-d]pyrimidin-4(3H)-one;
5-(3,5-difluorophenyl)-6-methyl-3-(2-oxo-2-(pyrrolidin-1-yl)ethyl)thieno[2,3-d]pyrimidin-4(3H)-one;
5-(3,5-diiodophenyl)-6-methyl-3-(2-oxo-2-(pyrrolidin-1-yl)ethyl)thieno[2,3-d]pyrimidin-4(3H)-one;
5-(3,5-bis(trifluoromethyl)phenyl)-6-methyl-3-(2-oxo-2-(pyrrolidin-1-yl)ethyl)thieno[2,3-d]pyrimidin-4(3H)-one;
5-(3,4-dibromophenyl)-6-methyl-3-(2-oxo-2-(pyrrolidin-1-yl)ethyl)thieno[2,3-d]pyrimidin-4(3H)-one;
and salts thereof.

21. The compound of claim 1, wherein $R^4$ is hydrogen.
22. The compound of claim 1, wherein Y is O.
23. The compound of claim 1, wherein Z is $CH_2$.
24. The compound of claim 1, wherein W is O.
25. The compound of claim 7, wherein the $R^5$ substituent at the 4-position relative to the ring atom of $R^2$ that connects to the rest of Formula I is halogen.
26. The compound of claim 8, wherein the at least one $R^5$ substituent at the 3- or 5-position relative to the ring atom of $R^2$ that connects to the rest of Formula I is halogen.

* * * * *